(12) United States Patent
Fischer et al.

(10) Patent No.: US 7,432,225 B2
(45) Date of Patent: Oct. 7, 2008

(54) SELECTIVE HERBICIDES BASED ON SUBSTITUTED CYCLIC KETO-ENOLS AND SAFENERS

(75) Inventors: Reiner Fischer, Monheim (DE); Mark Wilhelm Drewes, Langenfeld (DE); Dieter Feucht, Monheim (DE); Peter Dahmen, Neuss (DE); Rolf Pontzen, Leichlingen (DE)

(73) Assignee: Bayer CropScience AG, Monheim (DE)

( * ) Notice: Subject to any disclaimer, the term of this patent is extended or adjusted under 35 U.S.C. 154(b) by 642 days.

(21) Appl. No.: 10/485,909

(22) PCT Filed: Jul. 29, 2002

(86) PCT No.: PCT/EP02/08413

§ 371 (c)(1), (2), (4) Date: Aug. 6, 2004

(87) PCT Pub. No.: WO03/013249

PCT Pub. Date: Feb. 20, 2003

(65) Prior Publication Data

US 2005/0054535 A1    Mar. 10, 2005

(30) Foreign Application Priority Data

Aug. 10, 2001   (DE) ................. 101 39 465

(51) Int. Cl.
- *A01N 37/32* (2006.01)
- *A01N 43/34* (2006.01)
- *A01N 25/32* (2006.01)
- *C07D 231/06* (2006.01)
- *C07D 207/40* (2006.01)
- *A01N 31/00* (2006.01)
- *C07C 211/00* (2006.01)

(52) U.S. Cl. .............. 504/105; 504/246; 504/283; 504/262; 504/130; 548/543; 568/329

(58) Field of Classification Search ......... 504/103, 504/105, 130, 246, 262; 548/543; 568/329, 568/530
See application file for complete search history.

(56) References Cited

U.S. PATENT DOCUMENTS

| | | | |
|---|---|---|---|
| 4,175,135 A | 11/1979 | Haines | 424/311 |
| 4,209,532 A | 6/1980 | Wheeler | 424/331 |
| 4,256,657 A | 3/1981 | Wheeler | 260/465 D |
| 4,256,658 A | 3/1981 | Wheeler | 260/465 D |
| 4,256,659 A | 3/1981 | Wheeler | 260/465 D |
| 4,257,858 A | 3/1981 | Wheeler | 204/158 R |
| 4,283,348 A | 8/1981 | Wheeler | 260/465 D |
| 4,303,669 A | 12/1981 | D'Silva | 424/282 |
| 4,338,122 A | 7/1982 | Wheeler | 71/122 |
| 4,351,666 A | 9/1982 | Koerwer | 71/106 |
| 4,409,153 A | 10/1983 | Hodakowski | 260/946 |
| 4,422,870 A | 12/1983 | Wheeler | 71/106 |
| 4,436,666 A | 3/1984 | Wheeler | 260/455 B |
| 4,526,723 A | 7/1985 | Wheeler et al. | 260/410.5 |
| 4,551,547 A | 11/1985 | Wheeler | 560/255 |
| 4,613,617 A | 9/1986 | Sousa | 514/521 |
| 4,623,727 A | 11/1986 | Hübele | 546/178 |
| 4,632,698 A | 12/1986 | Wheeler | 71/106 |
| 4,639,266 A | 1/1987 | Heubach | 71/92 |
| 4,659,372 A | 4/1987 | Wheeler | 71/106 |
| 4,758,264 A | 7/1988 | Hubele | 71/94 |
| 4,785,105 A | 11/1988 | Hubele | 546/178 |
| 4,785,106 A | 11/1988 | Hubele | 546/178 |
| 4,822,884 A | 4/1989 | Hubele | 546/177 |
| 4,851,033 A | 7/1989 | Hubele | 71/94 |
| 4,881,966 A | 11/1989 | Nyffeler et al. | 71/94 |
| 4,891,057 A | 1/1990 | Sohn et al. | 71/72 |
| 4,902,340 A | 2/1990 | Hubele | 71/94 |

(Continued)

FOREIGN PATENT DOCUMENTS

CA    2 348 501    4/2001

(Continued)

OTHER PUBLICATIONS

J. Org. Chem., vol. 44, No1 26, (month unavailable) 1979, pp. 4906-4912, Thomas N. Wheeler, "Novel Photochemical Synthesis of 2-Aryl-1,3-cyclohexanediones".

*Primary Examiner*—Johann Richter
*Assistant Examiner*—Andriae M Holt
(74) *Attorney, Agent, or Firm*—Richard E. L. Henderson

(57) ABSTRACT

The present invention relates to selective herbicidal compositions comprising an effective amount of an active compound combination comprising
(a) at least one substituted cyclic ketoenol of the formula (I)

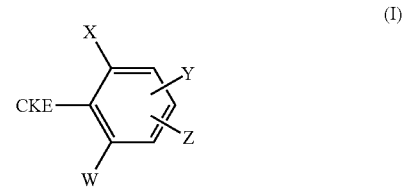

in which X, Z, W and Y and the group CKE are as defined in the disclosure,
and
(b) at least one compound which improves crop plant compatibility selected from the group of compounds listed in the description, particularly cloquintocet-mexyl and mefenpyr-diethyl.

The invention further relates to the use of these compositions as herbicides and to a method for controlling undesirable vegetation using these compositions.

4 Claims, No Drawings

U.S. PATENT DOCUMENTS

| | | | |
|---|---|---|---|
| 4,985,063 A | 1/1991 | Fischer et al. | 71/88 |
| 5,023,333 A | 6/1991 | Hubele | 546/175 |
| 5,045,107 A | 9/1991 | Hubele | 71/94 |
| 5,045,560 A | 9/1991 | Fischer et al. | 514/425 |
| 5,082,949 A | 1/1992 | Sohn et al. | 548/378 |
| 5,091,537 A | 2/1992 | Fischer et al. | 546/226 |
| 5,102,445 A | 4/1992 | Hubele | 71/94 |
| 5,116,836 A | 5/1992 | Fischer et al. | 514/224.2 |
| 5,142,065 A | 8/1992 | Fischer et al. | 548/533 |
| 5,186,737 A | 2/1993 | Fischer et al. | 504/283 |
| 5,225,434 A | 7/1993 | Bertram et al. | 514/411 |
| 5,258,527 A * | 11/1993 | Krauŝkopf et al. | 548/543 |
| 5,262,383 A | 11/1993 | Fischer et al. | 504/195 |
| 5,380,852 A | 1/1995 | Schütze et al. | 546/174 |
| 5,393,729 A | 2/1995 | Fischer et al. | 504/128 |
| 5,401,700 A | 3/1995 | Sohn et al. | 504/106 |
| 5,407,897 A | 4/1995 | Cary et al. | 504/108 |
| 5,462,913 A | 10/1995 | Fischer et al. | 504/138 |
| 5,504,057 A | 4/1996 | Fischer et al. | 504/283 |
| 5,516,750 A | 5/1996 | Willms et al. | 504/106 |
| 5,516,918 A | 5/1996 | Cary et al. | 549/23 |
| 5,567,671 A | 10/1996 | Fischer et al. | 504/283 |
| 5,589,469 A | 12/1996 | Fischer et al. | 514/91 |
| 5,602,078 A | 2/1997 | Fischer et al. | 504/283 |
| 5,610,122 A | 3/1997 | Fischer et al. | 504/251 |
| 5,616,536 A | 4/1997 | Fischer et al. | 504/225 |
| 5,622,917 A | 4/1997 | Fischer et al. | 504/283 |
| 5,677,449 A | 10/1997 | Fischer et al. | 544/165 |
| 5,696,050 A | 12/1997 | Cary et al. | 504/108 |
| 5,719,310 A | 2/1998 | Fischer et al. | 560/83 |
| 5,808,135 A | 9/1998 | Fischer et al. | 560/129 |
| 5,830,826 A | 11/1998 | Fischer et al. | 504/130 |
| 5,840,661 A | 11/1998 | Fischer et al. | 504/348 |
| 5,847,211 A | 12/1998 | Fischer et al. | 564/215 |
| 5,945,444 A | 8/1999 | Fischer et al. | 514/445 |
| 5,945,541 A | 8/1999 | Sohn et al. | 548/374.1 |
| 5,977,029 A | 11/1999 | Fischer et al. | 504/292 |
| 5,981,567 A | 11/1999 | Fischer et al. | 514/409 |
| 5,994,274 A | 11/1999 | Fischer et al. | 504/282 |
| 6,051,723 A | 4/2000 | Fischer et al. | 549/420 |
| 6,110,872 A | 8/2000 | Lieb et al. | 504/284 |
| 6,114,374 A | 9/2000 | Lieb et al. | 514/424 |
| 6,133,296 A | 10/2000 | Lieb et al. | 514/343 |
| 6,140,358 A | 10/2000 | Lieb et al. | 514/425 |
| 6,150,304 A | 11/2000 | Fischer et al. | 504/309 |
| 6,172,255 B1 | 1/2001 | Fischer et al. | 560/24 |
| 6,200,932 B1 * | 3/2001 | Fischer et al. | 504/225 |
| 6,251,830 B1 | 6/2001 | Fischer et al. | 504/251 |
| 6,251,833 B1 | 6/2001 | Erdelen et al. | 504/348 |
| 6,255,342 B1 | 7/2001 | Lieb et al. | 514/533 |
| 6,271,180 B2 | 8/2001 | Lieb et al. | 504/292 |
| 6,288,102 B1 | 9/2001 | Hagemann et al. | 514/409 |
| 6,316,486 B1 | 11/2001 | Lieb et al. | 514/411 |
| 6,358,887 B1 | 3/2002 | Fischer et al. | 504/284 |
| 6,359,151 B2 | 3/2002 | Lieb et al. | 549/265 |
| 6,380,246 B1 | 4/2002 | Lieb et al. | 514/462 |
| 6,388,123 B1 | 5/2002 | Lieb et al. | 560/76 |
| 6,391,912 B1 | 5/2002 | Hagemann et al. | 514/444 |
| 6,417,370 B1 | 7/2002 | Lieb et al. | 548/408 |
| 6,451,843 B1 | 9/2002 | Lieb et al. | 514/422 |
| 6,458,965 B1 | 10/2002 | Lieb et al. | 548/408 |
| 6,469,196 B2 | 10/2002 | Fischer et al. | 560/105 |
| 6,472,419 B1 | 10/2002 | Fischer et al. | 514/425 |
| 6,479,489 B1 | 11/2002 | Fischer et al. | 514/235.5 |
| 6,482,947 B1 | 11/2002 | Holdgrün et al. | 544/239 |
| 6,486,343 B1 | 11/2002 | Lieb et al. | 560/39 |
| 6,504,036 B1 | 1/2003 | Lieb et al. | 549/265 |
| 6,511,942 B1 | 1/2003 | Lieb et al. | 504/299 |
| 6,515,184 B1 | 2/2003 | Fischer et al. | 568/327 |
| 6,555,567 B1 | 4/2003 | Fischer et al. | 514/409 |
| 6,569,810 B1 | 5/2003 | Fischer et al. | 504/290 |
| 6,576,771 B1 | 6/2003 | Bretschneider et al. | 549/216 |
| 6,589,976 B1 | 7/2003 | Fischer et al. | 514/409 |
| 6,596,873 B1 | 7/2003 | Lieb et al. | 546/256 |
| 6,608,211 B1 | 8/2003 | Hagemann et al. | 548/410 |
| 6,630,594 B2 | 10/2003 | Hagemann et al. | 548/410 |
| 2001/0004528 A1 | 6/2001 | Lieb et al. | 504/292 |
| 2002/0010204 A1 | 1/2002 | Lieb et al. | 514/424 |
| 2002/0022575 A1 | 2/2002 | Fischer et al. | 504/221 |
| 2002/0072617 A1 | 6/2002 | Hagemann et al. | 548/541 |
| 2002/0161034 A1 | 10/2002 | Hagemann et al. | 514/432 |
| 2002/0188136 A1 | 12/2002 | Lieb et al. | 548/368.4 |
| 2003/0045432 A1 | 3/2003 | Fischer et al. | 504/221 |
| 2003/0073851 A1 | 4/2003 | Lieb et al. | 548/366.4 |
| 2003/0096806 A1 | 5/2003 | Lieb et al. | 514/212.01 |
| 2003/0144504 A1 | 7/2003 | Fischer et al. | 544/54 |
| 2003/0171219 A1 | 9/2003 | Lieb et al. | 504/221 |
| 2003/0199572 A1 | 10/2003 | Lieb et al. | 514/451 |
| 2003/0228984 A1 | 12/2003 | Hagemann et al. | 504/284 |

FOREIGN PATENT DOCUMENTS

| | | |
|---|---|---|
| CA | 2069901 C * | 10/2001 |
| EP | 346 260 | 12/1980 |
| EP | 0 456 063 | 11/1991 |
| EP | 442 077 | 11/1995 |
| JP | 2000-53670 | 2/2000 |
| JP | 2000-239276 | 9/2000 |
| WO | 96/21652 | 7/1996 |
| WO | 01/17972 | 3/2002 |

* cited by examiner

SELECTIVE HERBICIDES BASED ON SUBSTITUTED CYCLIC KETO-ENOLS AND SAFENERS

The present patent application has been filed under 35 U.S.C. 371 as a national stage application of PCT/EP02/08413, filed Jul. 29, 2002, which was published in German as International Patent Publication WO 03/013249 on Feb. 20, 2003, which is entitled to the right of priority of German Patent Application 101 39 465.9, filed Aug. 10,2001.

The invention relates to novel selective herbicidal active compound combinations which comprise substituted cyclic ketoenols, on the one hand, and at least one compound which improves crop plant compatibility, on the other, and which can be used with particularly good results for the selective control of weeds in various crops of useful plants.

Unsubstituted bicyclic 3-arylpyrrolidine-2,4-dione derivatives (EP-A-355 599, EP-A-415 211 and JP 12-053 670) and substituted monocyclic 3-arylpyrrolidine-2,4-dione derivatives (EP-A-377 893 and EP-A-442 077) having herbicidal action are already known.

Also known are polycyclic 3-arylpyrrolidine-2,4-dione derivatives (EP-A-442 073) and 1H-arylpyrrolidinedione derivatives (EP-A-456 063, EP-A-521 334, EP-A-596 298, EP-A-613 884, EP-A-613 885, WO 95/01358, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/16748, WO 99/24437, WO 99/43649, WO 99/48869, WO 99/55673, WO 01/17972 and WO 01/23354).

Also known are 3-aryl-$\Delta^3$-dihydrofuranone derivatives having herbicidal properties, from EP-A-528 156, EP-A-0 647 637, WO 95/26 345, WO 96/20 196, WO96/25 395, WO, 96/35 664, WO 97/01 535, WO 97/02 243, WO 97/368 68, WO 98/05638, WO 98/25928, WO 99/16748, WO 99/43649, WO 99/48869, WO 99/55673, JP 12-239 276 and WO 01/17972. 3-Aryl-$\Delta^3$-dihydrothiophenone derivatives, too, are known (WO 95/26 345, WO 96/25 395, WO 97/01 535, WO 97/02 243, WO 97/36 868, WO 98/05638, WO 98/25928, WO 99/16748, WO 99/43649, WO 99/48869, WO 99/55673, WO 01/17972, WO 01/23354).

Phenylpyrone derivatives which are substituted in the phenyl ring and have herbicidal properties are described in EP-A-588 137, WO 96/25 395, WO 96/35 664, WO 97/01 535, WO 97/02 243, WO 97/16 436, WO 97/19 941, WO 97/36 868, WO 98/05638, WO 99/43649, WO 99/48869, WO 99/55673 and WO 01/17972.

It is known that certain substituted 2-arylcyclopentanediones have herbicidal properties (cf. for example, U.S. Pat. Nos. 4,283,348; 4,338,122; 4,436,666; 4,526,723; 4,551,547; 4,632,698; WO 96/01 798; WO 96/03 366, WO 97/14 667 and also WO 98/39281, WO 99/43649, WO 99/48869, WO 99/55673 and WO 01/17972).

Moreover, it is known that certain substituted 2-arylcyclohexanediones have herbicidal and acaricidal properties (U.S. Pat. Nos. 4,175,135, 4,209,532, 4,256,657, 4,256,658, 4,256,659, 4,257,858, 4,283,348, 4,303,669, 4,351,666, 4,409,153, 4,436,666, 4,526,723, 4,613,617, 4,659,372, DE-A 2 813 341, and also Wheeler, T. N., J. Org. Chem. 44, 4906 (1979), WO 99/43649, WO 99/48869, WO 99/55673 and WO 01/17972).

However, the activity of these compounds and/or their compatibility with crop plants are not under all conditions entirely satisfactory.

Surprisingly, it has now been found that certain substituted cyclic ketoenols, when used together with the compounds (safeners/antidotes) described below which improve crop plant compatibilty, prevent damage to the crop plants extremely well and can be used particularly advantageously as broad-spectrum combination preparations for the selective control of undesirable plants in crops of useful plants, such as, for example, in cereals, but also in maize, soya beans and rice.

The invention provides selective herbicidal combinations comprising an effective amount of an active compound combination comprising (a) at least one substituted cyclic ketoenol of the formula (I)

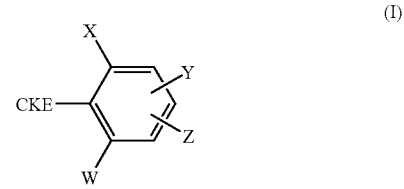

(I)

in which

X represents halogen, alkyl, alkenyl, alkinyl, alkoxy, alkenyloxy, alkylthio, alkylsulphinyl, alkylsulphonyl, haloalkyl, haloalkoxy, haloalkenyloxy, nitro or cyano, Z represents hydrogen, in each case optionally substituted alkenyl, alkinyl, aryl or represents hetaryl, W and Y independently of one another represent hydrogen, halogen, alkyl, alkoxy, alkenyloxy, haloalkyl, haloalkoxy, haloalkenyloxy, nitro or cyano, with the proviso that, if Y represents 4-methyl, W and X do not simultaneously represent ethyl or W does not represent methoxy or difluoromethoxy if X represents ethyl, CKE represents one of the groups

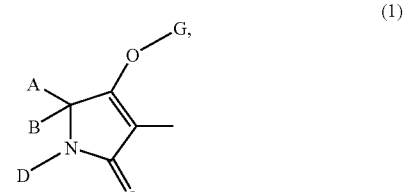

(1)

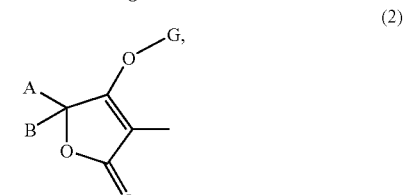

(2)

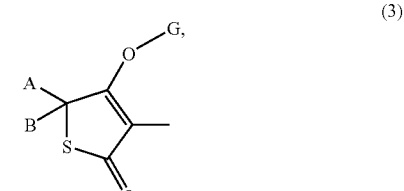

(3)

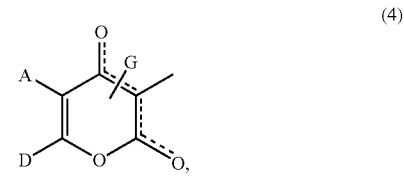

(4)

-continued

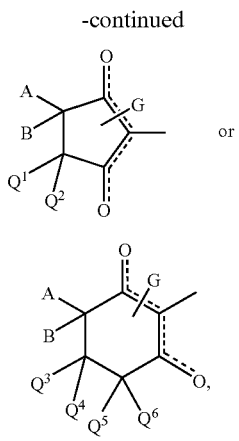

(5) or (6)

in which
A represents hydrogen, in each case optionally halogen-substituted alkyl, alkenyl, alkoxyalkyl, alkylthioalkyl, saturated or unsaturated, optionally substituted cycloalkyl, in which optionally at least one ring atom is replaced by a heteroatom, or in each case optionally halogen-, alkyl-, haloalkyl-, alkoxy-, haloalkoxy-, cyano- or nitro-substituted aryl, arylalkyl or hetaryl, B represents hydrogen, alkyl or alkoxyalkyl, or A and B together with the carbon atom to which they are attached represent a saturated or unsaturated, unsubstituted or substituted cycle which optionally contains at least one heteroatom, D represents hydrogen or an optionally substituted radical from the group consisting of alkyl, alkenyl, alkinyl, alkoxyalkyl, saturated or unsaturated cycloalkyl, in which optioinally one or more ring members are replaced by heteroatoms, arylalkyl, aryl, hetarylalkyl or hetaryl, or A and D together with the atoms to which they are attached represent a saturated or unsaturated cycle which is unsubstituted or substituted in the A,D moiety and optionally contains at least one heteroatom, or A and $Q^1$ together represent alkanediyl or alkenediyl which are in each case optionally substituted by hydroxyl or by in each case optionally substituted alkyl, alkoxy, alkylthio, cycloalkyl, benzyloxy or aryl, or $Q^1$ represents hydrogen or alkyl, $Q^2$, $Q^4$, $Q^5$ and $Q^6$ independently of one another represent hydrogen or alkyl, $Q^3$ represents hydrogen, alkyl, alkoxyalkyl, alkylthioalkyl, optionally substituted cycloalkyl (in which optionally one methylene group is replaced by oxygen or sulphur) or optionally substituted phenyl, or $Q^3$ and $Q^4$ together with the carbon atom to which they are attached, represent a saturated or unsaturated, unsubstituted or substituted cycle which optionally contains a heteroatom, G represents hydrogen (a) or represents one of the groups

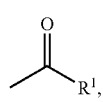

(b)

-continued

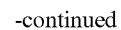
(c)

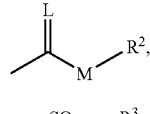
,

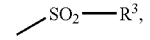
(d)

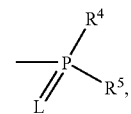
,

(e)

E or
(f)

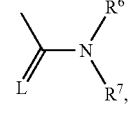
,
(g)

in which
E represents a metal ion equivalent or an ammonium ion,
L represents oxygen or sulphur,
M represents oxygen or sulphur,
$R^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl, which may be interrupted by at least one heteroatom, represents in each case optionally substituted phenyl, phenylalkyl, hetaryl, phenoxyalkyl or hetaryloxyalkyl,
$R^2$ represents in each case optionally halogen-substituted alkyl, alkenyl, alkoxyalkyl, polyalkoxyalkyl or represents in each case optionally substituted cycloalkyl, phenyl or benzyl,
$R^3$, $R^4$ and $R^5$ independently of one another represent in each case optionally halogen-substituted alkyl, alkoxy, alkylamino, dialkylamino, alkylthio, alkenylthio, cycloalkylthio and represent in each case optionally substituted phenyl, benzyl, phenoxy or phenylthio,
$R^6$ and $R^7$ independently of one another represent hydrogen, in each case optionally halogen-substituted alkyl, cycloalkyl, alkenyl, alkoxy, alkoxyalkyl, represent optionally substituted phenyl, represent optionally substituted benzyl, or together with the N atom to which they are attached represent a cycle which is optionally interrupted by oxygen or sulphur, including all possible tautomeric forms of the compounds of the general formula (I) and the possible salts or acid or base adducts of the compounds of the general formula (I) and (b) at least one compound which improves crop plant compatibility, from the group of compounds below:
4-dichloroacetyl-1-oxa-4-aza-spiro[4.5]-decane (AD-67, MON-4660), 1-dichloro-acetyl-hexahydro-3,3,8a-trimethylpyrrolo[1,2-a]-pyrimidin-6(2H)-one (dicyclonon, BAS-145138), 4-dichloroacetyl-3,4-dihydro-3-methyl-2H-1,4-benzoxazine (benoxacor), 1-methyl-hexyl 5-chloro-quinolin-8-oxy-acetate (cloquintocet-mexyl— cf. also related compounds in EP-A-86750, EP-A-94349, EP-A-191736, EP-A-492366), 3-(2-chloro-benzyl)-1-(1-methyl-1-phenyl-ethyl)-urea (cumyluron), α-(cyano-methoximino)-phenylacetonitrile (cyometrinil), 2,4-dichloro-phenoxyacetic acid (2,4-D), 4-(2,4-dichloro-phenoxy)-butyric acid (2,4-DB), 1-(1-methyl-1-phenyl-ethyl)-3-(4-methyl-phenyl)-urea (daimuron, dymron), 3,6- dichloro-2-methoxy-benzoic acid (dicamba), S-1-methyl-1-phenyl-ethyl piperidine-1-thiocarboxylate (dimepiperate), 2,2-dichloro-N-(2-oxo-2-(2-propenylamino)-ethyl)-N-(2-propenyl)-acetamide (DKA-24), 2,2-dichloro-N,N-di-2-propenyl-acetamide (dichlormid), 4,6-dichloro-2-phenyl-pyrimidine (fenclorim), ethyl 1-(2,4-dichloro-phenyl)-5-trichloromethyl-1H-1,2,4-triazole-3-carboxylate (fenchlorazole-ethyl—cf. also related compounds in EP-A-174562 and EP-A-346620), phenylmethyl 2-chloro-4-trifluoromethyl-thiazole-5-carboxylate (flurazole), 4-chloro-N-(1,3-dioxolan-2-yl-methoxy)-α-trifluoro-acetophenone oxime (fluxofenim), 3-dichloro-acetyl-5-(2-furanyl)-2,2-dimethyl-oxazolidine (furilazole, MON-13900), ethyl 4,5-dihydro-5,5-diphenyl-3-isoxazolecarboxylate (isoxadifen-ethyl—cf. also related compounds in WO-A-95/07897), 1-(ethoxycarbonyl)-ethyl 3,6-dichloro-2-methoxybenzoate (lactidichlor), (4-chloro-o-tolyloxy)-acetic acid (MCPA), 2-(4-chloro-o-tolyloxy)-propionic acid (mecoprop), diethyl 1-(2,4-dichloro-phenyl)-4,5-dihydro-5-methyl-1H-pyrazole-3,5-dicarboxylate (mefenpyr-diethyl—cf. also related compounds in WO-A-91/07874), 2-dichloromethyl-2-methyl-1,3-dioxolane (MG-191), 2-propenyl-1-oxa-4-azaspiro[4.5]decane 4-carbodithioate (MG-838), 1,8-naphthalic anhydride, α-(1,3-dioxolan-2-yl-methoximino)-phenylacetonitrile (oxabetrinil), 2,2-dichloro-N-(1,3-dioxolan-2-yl-methyl)-N-(2-propenyl)-acetamide (PPG-1292), 3-dichloroacetyl-2,2-dimethyl-oxazolidine (R-28725), 3-dichloroacetyl-2,2,5-trimethyl-oxazolidine (R-29148), 4-(4-chloro-o-tolyl)-butyric acid, 4-(4-chloro-phenoxy)-butyric acid, diphenylmethoxyacetic acid, methyl diphenylmethoxyacetate, ethyl diphenyl-methoxyacetate, methyl 1-(2-chloro-phenyl)-5-phenyl-1H-pyrazole-3-carboxylate, ethyl 1-(2,4-dichloro-phenyl)-5-methyl-1H-pyrazole-3-carboxylate, ethyl 1-(2,4-dichloro-phenyl)-5-isopropyl-1H-pyrazole-3-carboxylate, ethyl 1-(2,4-dichloro-phenyl)-5-(1,1-dimethyl-ethyl)-1H-pyrazole-3-carboxylate, ethyl 1-(2,4-dichloro-phenyl)-5-phenyl-1H-pyrazole-3-carboxylate (cf also related compounds in EP-A-269806 and EP-A-333131), ethyl 5-(2,4-dichloro-benzyl)-2-isoxazoline-3-carboxylate, ethyl 5-phenyl-2-isoxazoline-3-carboxylate, ethyl 5-(4-fluoro-phenyl)-5-phenyl-2-isoxazoline-3-carboxylate (cf. also related compounds in WO-A-91/08202), 1,3-dimethyl-but-1-yl 5-chloro-quinolin-8-oxy-acetate, 4-allyloxy-butyl 5-chloro-quinolin-8-oxy-acetate, 1-allyloxy-prop-2-yl 5-chloro-quinolin-8-oxy-acetate, methyl 5-chloro-quinoxalin-8-oxy-acetate, ethyl 5-chloro-quinolin-8-oxy-acetate, allyl 5-chloro-quinoxalin-8-oxy-acetate, 2-oxo-prop-1-yl 5-chloro-quinolin-8-oxy-acetate, diethyl 5-chloro-quinolin-8-oxy-malonate, diallyl 5-chloro-quinoxalin-8-oxy-malonate, diethyl 5-chloro-quinolin-8-oxy-malonate (cf. also related compounds in EP-A-582198), 4-carboxy-chroman-4-yl-acetic acid (AC-304415, cf. EP-A-613618), 4-chloro-phenoxy-acetic acid, 3,3'-dimethyl-4-methoxy-benzophenone, 1-bromo-4-chloromethylsulphonyl-benzene, 1-[4-(N-2-methoxybenzoylsulphamoyl)-phenyl]-3-methyl-urea (alias N-(2-methoxy-benzoyl)-4-[(methylamino-carbonyl)-amino]-benzenesulphonamide), 1-[4-(N-2-methoxybenzoylsulphamoyl)-phenyl]-3,3-dimethyl-urea, 1-[4-(N-4,5-dimethylbenzoylsulphamoyl)-phenyl]-3-methyl-urea, 1-[4-(N-naphthylsulphamoyl)-phenyl]-3,3-dimethyl-urea, N-(2-methoxy-5-methyl-benzoyl)-4-(cyclopropylaminocarbonyl)-benzenesulphonamide, and/or one of the following compounds defined by general formulae of the general formula (IIa)

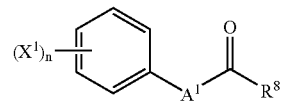

or of the general formula (IIb)

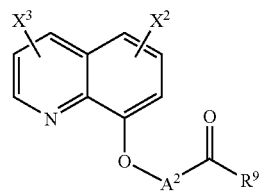

or the formula (IIc)

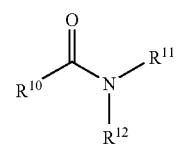

where n represents a number between 0 and 5, $A^1$ represents one of the divalent heterocyclic groupings shown below

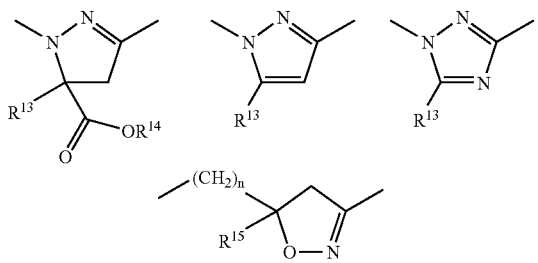

$A^2$ represents optionally $C_1$-$C_4$-alkyl- and/or $C_1$-$C_4$-alkoxy-carbonyl-substituted alkanediyl with 1 or 2 carbon atoms, $R^8$ represents hydroxyl, mercapto, amino, $C_1$-$C_6$-alkoxy, $C_1$-$C_6$-alkylthio, $C_1$-$C_6$-alkylamino or di-($C_1$-$C_4$-alkyl)-amino, $R^9$ represents hydroxyl, mercapto, amino, $C_1$-$C_6$-alkoxy, $C_1$-$C_6$-alkylthio, $C_1$-$C_6$-alkylamino or di-($C_1$-$C_4$-alkyl)-amino, $R^{10}$ represents in each case optionally fluorine-, chlorine- and/or bromine-substituted $C_1$-$C_4$-alkyl, $R^{11}$ represents hydrogen, in each case optionally fluorine-, chlorine- and/or bromine-substituted $C_1$-$C_6$-alkyl, $C_2$-$C_6$-alkenyl or $C_2$-$C_6$-alkinyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{12}$ represents hydrogen, in each case optionally fluorine-, chlorine- and/or bromine-substituted $C_1$-$C_6$-alkyl, $C_2$-$C_6$-alkenyl or $C_2$-$C_6$-alkinyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, or together with $R^{11}$ represents $C_3$-$C_6$-alkanediyl or $C_2$-$C_5$-oxaalkanediyl, each of which is optionally substituted by $C_1$-$C_4$-alkyl, phenyl, furyl, a fused-on benzene ring or by two substituents which together with the C atom to which they are attached form a 5- or 6-membered carbocycle, $R^{13}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $R^{14}$ represents hydrogen, optionally hydroxyl-, cyano-, halogen- or $C_1$-$C_4$-alkoxy-substituted $C_1$-$C_6$-alkyl, $C_3$-$C_6$-cycloalkyl or tri-($C_1$-$C_4$-alkyl)-silyl, $R^{15}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or the following compounds defined by general formulae of the general formula (IId)

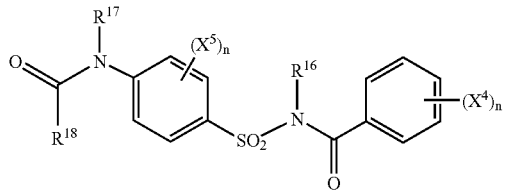

(IId)

or of the general formula (IIe)

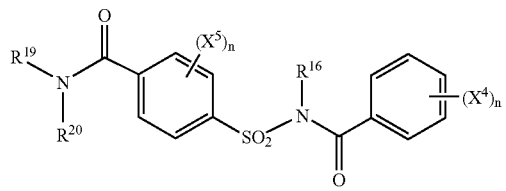

(IIe)

where n represents a number between 0 and 5, $R^{16}$ represents hydrogen or $C_1$-$C_4$-alkyl, $R^{17}$ represents hydrogen or $C_1$-$C_4$-alkyl, $R^{18}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di-($C_1$-$C_4$-alkyl)-amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{19}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkinyl, or optionally cyano-, halogen- or $C_1$-$C_4$-alkyl-substituted $C_3$-$C_6$-cycloalkyl, $R^{20}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkinyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or together with $R^{19}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

In the definitions, the hydrocarbon chains, such as an alkyl or alkanediyl, are in each case straight-chain or branched—including in combination with heteroatoms, such as in alkoxy.

Depending inter alia on the nature of the substituents, the compounds of the formula (I) can be present as geometrical and/or optical isomers or isomer mixtures of varying composition which, if appropriate, can be separated in a customary manner. The present invention provides both the pure isomers and the isomer mixtures, and their use and the compositions comprising them. However, for the sake of simplicity, hereinbelow only compounds of the formula (I) are referred to, although what is meant are both the pure compounds and, if appropriate, also mixtures having various proportions of isomeric compounds.

Including the meanings (1) to (6) of the groupe CKE, the following principal structures (I-1) to (I-6) result:

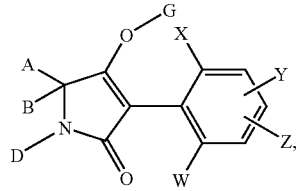

(I-1)

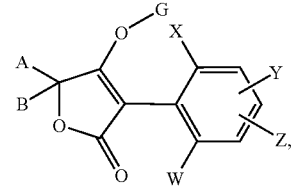

(I-2)

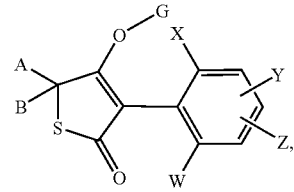

(I-3)

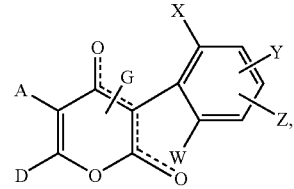

(I-4)

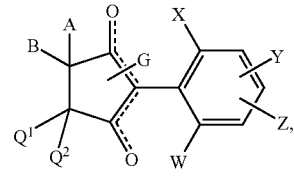

(I-5)

-continued (I-6)

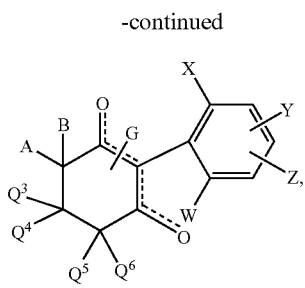

in which

A, B, D, G, Q$^1$, Q$^2$, Q$^3$, Q$^4$, Q$^5$, Q$^6$, W, X, Y and Z are as defined above.

Including the different meanings (a), (b), (c), (d), (e), (f) and (g) of the group G, the following principal structures (I-1-a) to (I-1-g) result if CKE represents the group (1), (I-1-a):

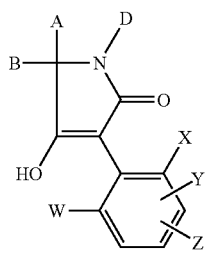

(I-1-b):

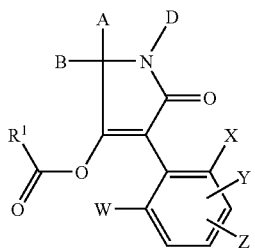

(I-1-c):

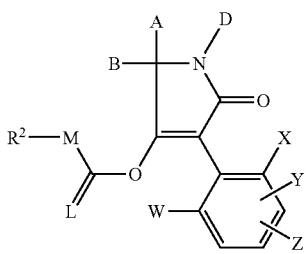

(I-1-d):

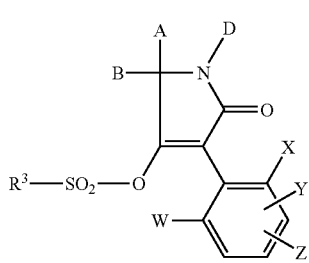

(I-1-e):

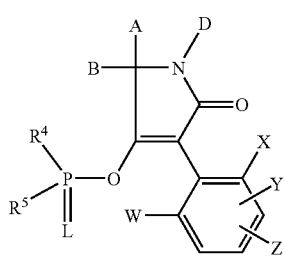

(I-1-f):

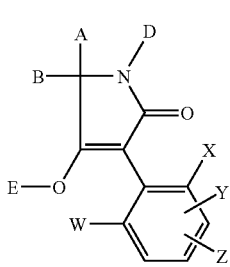

(I-1-g):

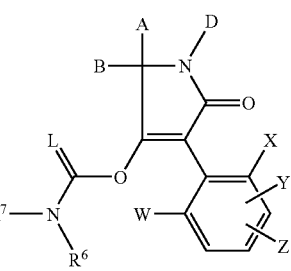

in which

A, B, D, E, L, M, W, X, Y, Z, R$^1$, R$^2$, R$^3$, R$^4$, R$^5$, R$^6$ and R$^7$ are as defined above.

Including the different meanings (a), (b), (c), (d), (e), (f) and (g) of the group G, the following principal structures (I-2-a) to (I-2-g) result if CKE represents the group (2)

(I-2-a):

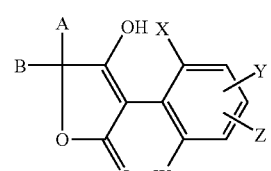

(I-2-b):

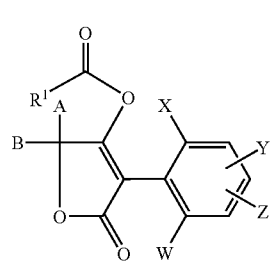

-continued
(I-2-c):
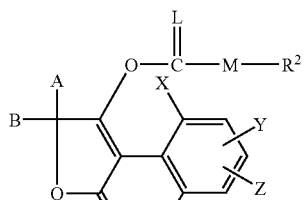
(I-2-d):
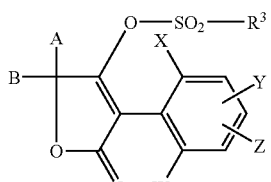
(I-2-e):
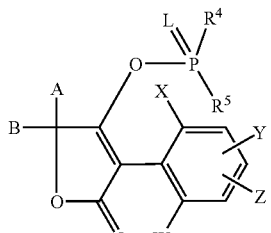
(I-2-f):
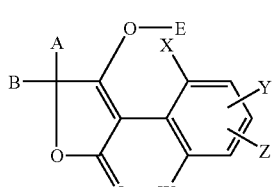
(I-2-g):
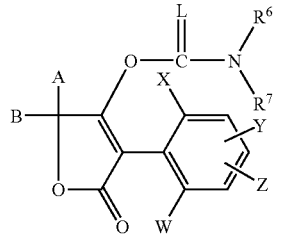
in which
A, B, E, L, M, W, X, Y, Z, $R^1$, $R^2$, $R^3$, $R^4$, $R^5$, $R^6$ and $R^7$ are as defined above.
Including the different meanings (a), (b), (c), (d), (e), (f) and (g) of the group G, the following principal structures (I-3-a) to (I-3-g) result if CKE represents the group (3)
(I-3-a):
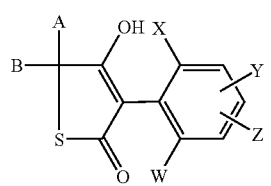
(I-3-b):
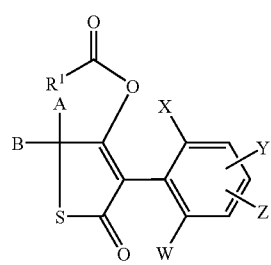
(I-3-c):
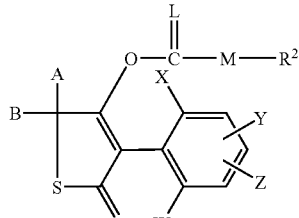
(I-3-d):
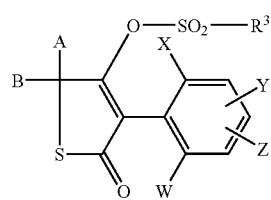
(I-3-e):
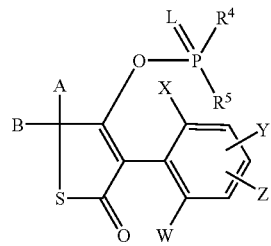
(I-3-f):
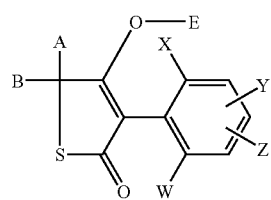
(I-3-g):
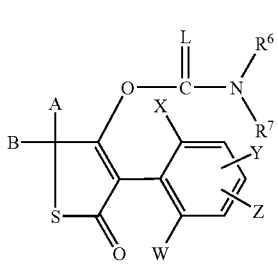

in which

A, B, E, L, M, W, X, Y, Z, R¹, R², R³, R⁴, R⁵, R⁶ and R⁷ are as defined above.

Depending on the position of the substituent G, the compounds of the formula (I-4) can be present in the two isomeric forms of the formulae (I-4-A) and (I-4-B)

(I-4-A)

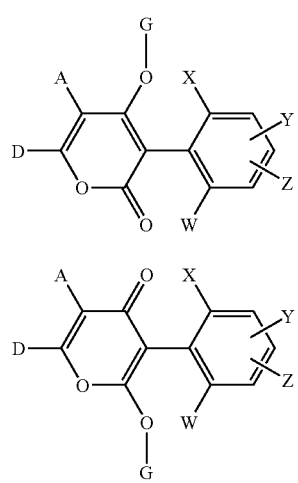

(I-4-B)

which is meant to be indicated by the broken line in formula (I-4).

The compounds of the formulae (I-4-A) and (I-4-B) can be present both as mixtures and in the form of their pure isomers. Mixtures of the compounds of the formulae (I-4-A) and (I-4-B) can, if appropriate, be separated in a manner known per se by physical methods, for example by chromatographic methods.

For reasons of clarity, hereinbelow only one of the possible isomers is shown in each case. This does not exclude that the compounds may, if appropriate, be present in the form of the isomer mixtures or in the respective other isomeric form.

Including the different meanings (a), (b), (c), (d), (e), (f) and (g) of the group G, the following principal structures (I-4-a) to (I-4-g) result if CKE represents the group (4)

(I-4-a):

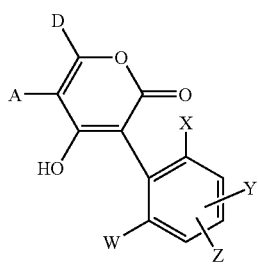

(I-4-b):

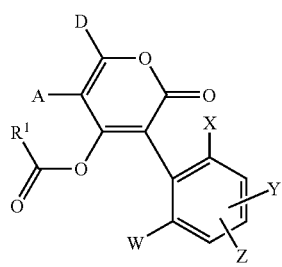

-continued (I-4-c):

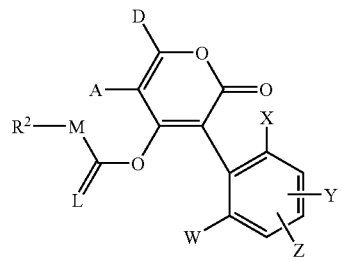

(I-4-d):

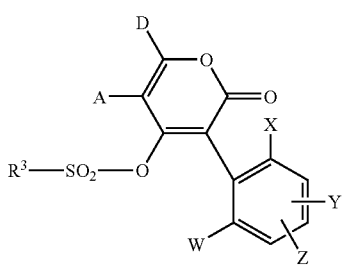

(I-4-e):

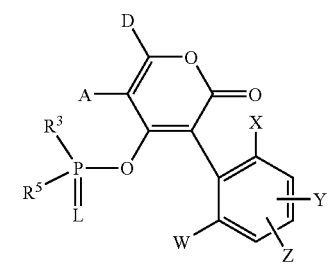

(I-4-f):

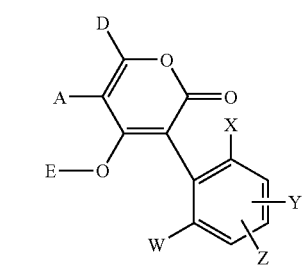

(I-4-g):

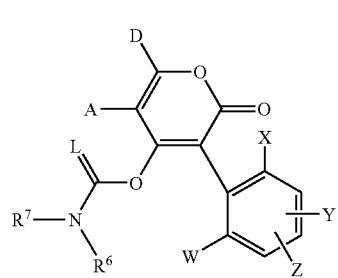

in which

A, D, E, L, M, W, X, Y, Z, R¹, R², R³, R⁴, R⁵, R⁶ and R⁷ are as defined above.

Depending on the position of the substituent G, the compounds of the formula (I-5) can be present in the two isomeric forms of the formulae (I-5-A) and (I-5-B)

(I-5-A)

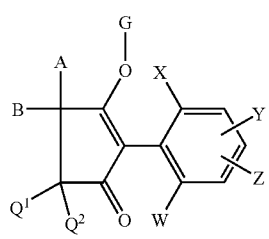

(I-5-B)

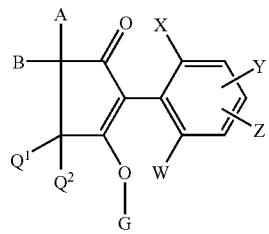

which is meant to be indicated by the broken line in the formula (I-5).

The compounds of the formulae (I-5-A) and (I-5-B) can be present both as mixtures and in the form of their pure isomers. Mixtures of the compounds of the formulae (I-5-A) and (I-5-B) can, if appropriate, be separated by physical methods, for example by chromatographic methods.

For reasons of clarity, hereinbelow only one of the possible isomers is shown in each case. This does not exclude that the compounds may, if appropriate, be present in the form of the isomer mixtures or in the respective other isomeric form.

Including the different meanings (a), (b), (c), (d), (e), (f) and (g) of the group G, the following principal structures (I-5-a) to (I-5-g) result:

(I-5-a):

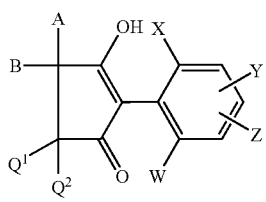

(I-5-b):

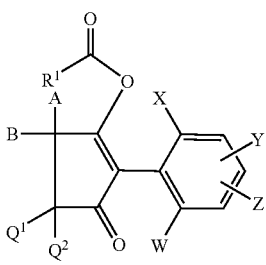

(I-5-c):

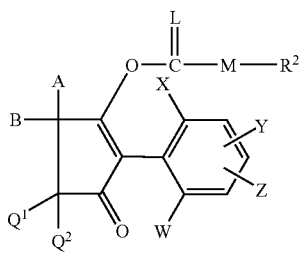

(I-5-d):

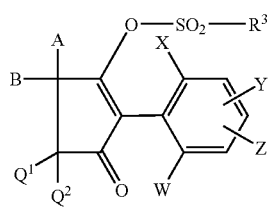

(I-5-e):

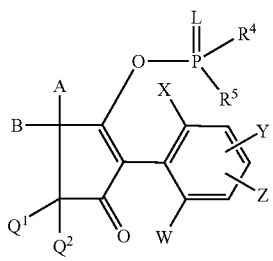

(I-5-f):

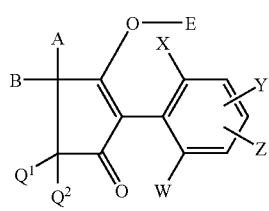

(I-5-g):

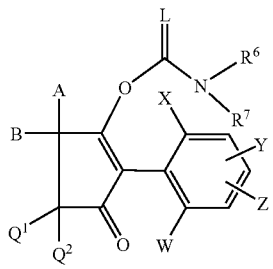

in which

A, B, $Q^1$, $Q^2$, E, L, M, W, X, Y, Z, $R^1$, $R^2$, $R^3$, $R^4$, $R^5$, $R^6$ and $R^7$ are as defined above.

Depending on the position of the substituent G, the compounds of the formula (I-6) can be present in the two isomeric forms of the formulae (I-6-A) and (I-6-B) which is meant to be indicated by the broken line in the formula (I-6):

(I-6-A)

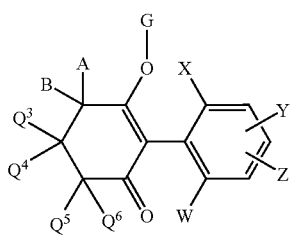

(I-6-B)

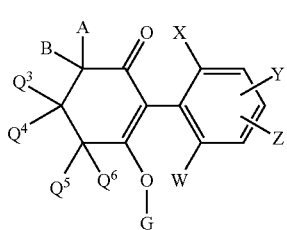

(I-6-d):

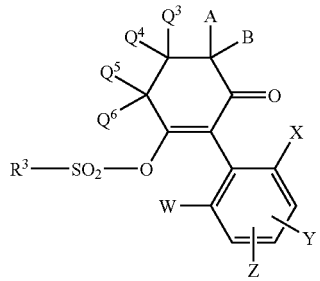

The compounds of the formulae (I-6-A) and (I-6-B) can be present both as mixtures and in the form of their pure isomers. Mixtures of the compounds of the formulae (I-6-A) and (I-6-B) may, if appropriate, be separated by physical methods, for example by chromatographic methods.

For reasons of clarity, hereinbelow only one of the possible isomers is shown in each case. This includes that the compound in question may, if appropriate, be present as an isomer mixture or in the respective other isomeric form.

Including the different meanings (a), (b), (c), (d), (e), (f) and (g) of the group G, the following principal structures (I-6-a) to (I-6-g) result:

(I-6-e):

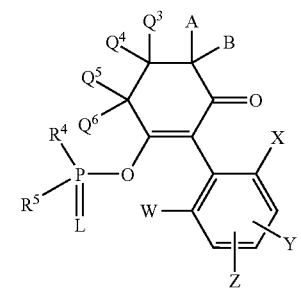

(I-6-a):

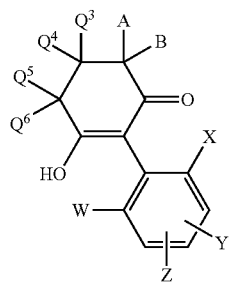

(I-6-f):

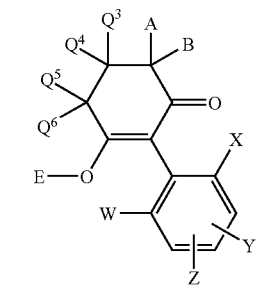

(I-6-b):

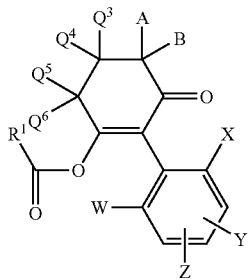

(I-6-g):

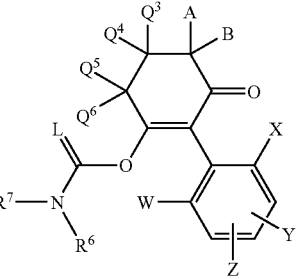

(I-6-c):

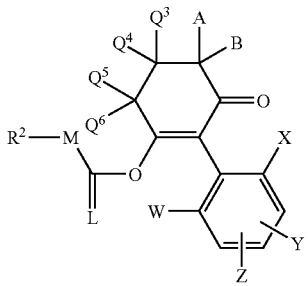

in which
A, B, E, L, M, $Q^3$, $Q^4$, $Q^5$, $Q^6$, W, X, Y, Z, $R^1$, $R^2$, $R^3$, $R^4$, $R^5$, $R^6$ and $R^7$ are as defined above.

The formula (I) provides a general definition of the substituted cyclic ketoenols according to the invention of the herbicidal compositions. Preferred substituents and ranges of the radicals given in the formulae mentioned above and below are illustrated below:

X preferably represents halogen, $C_1$-$C_6$-alkyl, $C_2$-$C_6$-alkenyl, $C_1$-$C_6$-haloalkyl, $C_1$-$C_6$-alkoxy, $C_3$-$C_6$-alkenyloxy, $C_1$-$C_6$-haloalkoxy, $C_3$-$C_6$-haloalkenyloxy, nitro or cyano, Z preferably represents hydrogen, $C_2$-$C_6$-alkenyl, $C_2$-$C_6$-alkinyl or represents one of the radicals

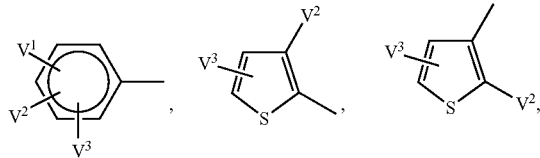

in which $V^1$ represents hydrogen, halogen, $C_1$-$C_{12}$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_4$-haloalkyl, $C_1$-$C_4$-haloalkoxy, nitro or cyano, $V^2$ and $V^3$ independently of one another represent hydrogen, halogen, $C_1$-$C_6$-alkyl, $C_1$-$C_6$-alkoxy, $C_1$-$C_4$-haloalkyl or $C_1$-$C_4$-haloalkoxy, W and Y independently of one another preferably represent hydrogen, halogen, $C_1$-$C_6$-alkyl, $C_1$-$C_6$-haloalkyl, $C_1$-$C_6$-alkoxy, $C_1$-$C_6$-haloalkoxy, nitro or cyano, with the proviso that, if Y represents 4-methyl, W and X do not simultaneously represent ethyl or W does not represent methoxy or difluoromethoxy if X represents ethyl.

CKE preferably represents one of the groups

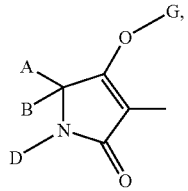 (1)

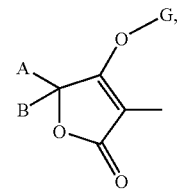 (2)

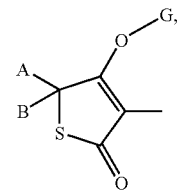 (3)

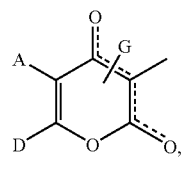 (4)

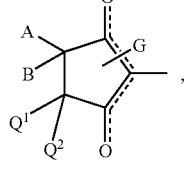 (5)

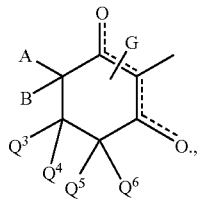 (6)

A preferably represents hydrogen or in each case optionally halogen-substituted $C_1$-$C_{12}$-alkyl, $C_3$-$C_8$-alkenyl, $C_1$-$C_{10}$-alkoxy-$C_1$-$C_8$-alkyl, $C_1$-$C_{10}$-alkylthio-$C_1$-$C_6$-alkyl, optionally halogen-, $C_1$-$C_6$-alkyl- or $C_1$-$C_6$-alkoxy-substituted $C_3$-$C_8$-cycloalkyl, in which optionally one or two not directly adjacent ring members are replaced by oxygen and/or sulphur or represents in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl or phenyl-$C_1$-$C_6$-alkyl.

B preferably represents hydrogen, $C_1$-$C_{12}$-alkyl or $C_1$-$C_8$-alkoxy-$C_1$-$C_6$-alkyl, or A, B and the carbon atom to which they are attached preferably represent saturated $C_3$-$C_{10}$-cycloalkyl or unsaturated $C_5$-$C_{10}$-cycloalkyl in which optionally one ring member is replaced by oxygen or sulphur and which are optionally mono- or disubstituted by $C_1$-$C_8$-alkyl, $C_3$-$C_{10}$-cycloalkyl, $C_1$-$C_8$-haloalkyl, $C_1$-$C_8$-alkoxy, $C_1$-$C_8$-alkylthio, halogen or phenyl, or A, B and the carbon atom to which they are attached preferably represent $C_3$-$C_6$-cycloalkyl which is substituted by an alkylenediyl or by an alkylenedioxyl or by an alkylenedithioyl group which, with the carbon atom to which it is attached, forms a further five- to eight-membered ring and which is optionally substituted by $C_1$-$C_4$-alkyl which optionally contain one or two not directly adjacent oxygen and/or sulphur atoms, or A, B and the carbon atom to which they are attached preferably represent $C_3$-$C_8$-cycloalkyl or $C_5$-$C_8$-cycloalkenyl in which two substituents together with the carbon atoms to which they are attached represent in each case optionally $C_1$-$C_6$-alkyl-, $C_1$-$C_6$-alkoxy- or halogen-substituted $C_2$-$C_6$-alkanediyl, $C_2$-$C_6$-alkenediyl or $C_4$-$C_6$-alkanedienediyl in which optionally one methylene group is replaced by oxygen or sulphur.

D preferably represents hydrogen, in each case optionally halogen-substituted $C_1$-$C_{12}$-alkyl, $C_3$-$C_8$-alkenyl, $C_3$-$C_8$-alkinyl, $C_1$-$C_{10}$-alkoxy-$C_2$-$C_8$-alkyl, optionally halogen-, $C_1$-$C_4$-alkyl-, $C_1$-$C_4$-alkoxy- or $C_1$-$C_4$-haloalkyl-substituted $C_3$-$C_8$-cycloalkyl, in which optionally one ring member is replaced by oxygen or sulphur or in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl or phenyl-$C_1$-$C_6$-alkyl.

A and D together preferably represent in each case optionally substituted $C_3$-$C_6$-alkanediyl or $C_3$-$C_6$-alkenediyl in which optionally one methylene group is replaced by a carbonyl group, by oxygen or by sulphur, possible substituents being in each case:

halogen, hydroxyl, mercapto or in each case optionally halogen-substituted $C_1$-$C_{10}$-alkyl or $C_1$-$C_6$-alkoxy, or a further $C_3$-$C_6$-alkanediyl grouping, $C_3$-$C_6$-alkenediyl grouping or a butadienyl grouping which is optionally substituted by $C_1$-$C_6$-alkyl or in which optionally two adjacent substituents together with the carbon atoms to which they are attached form a further saturated or unsaturated cycle having 5 or 6 ring atoms (in the case of the compound of the formula (I-1), A and D together with the atoms to which they are attached then represent, for example, the groups AD-1 to AD-10 mentioned further below), which may contain oxygen or sulphur.

A and $Q^1$ together preferably represent $C_3$-$C_6$-alkanediyl or $C_4$-$C_6$-alkenediyl, each of which is optionally mono- or disubstituted by identical or different halogens, by $C_1$-$C_{10}$-alkyl, $C_1$-$C_6$-alkoxy, $C_1$-$C_6$-alkylthio or $C_3$-$C_7$-cycloalkyl, each of which is optionally mono- to trisubstituted by identical or different halogens, or by benzyloxy or phenyl, each of which is optionally mono- to trisubstituted by identical or different substituents from the group consisting of halogen, $C_1$-$C_6$-alkyl and $C_1$-$C_6$-alkoxy in which $C_3$-$C_6$-alkanediyl or $C_4$-$C_6$-alkenediyl is furthermore bridged by a $C_1$-$C_2$-alkanediyl group or by an oxygen atom, or $Q^1$ preferably represents hydrogen or $C_1$-$C_4$-alkyl.

$Q^2$, $Q^4$, $Q^5$ and $Q^6$ independently of one another preferably represent hydrogen or $C_1$-$C_4$-alkyl.

$Q^3$ preferably represents hydrogen, $C_1$-$C_6$-alkyl, $C_1$-$C_6$-alkoxy-$C_1$-$C_2$-alkyl, $C_1$-$C_6$-alkylthio-$C_1$-$C_2$-alkyl, optionally halogen-, $C_1$-$C_4$-alkyl- or $C_1$-$C_4$-alkoxy-substituted $C_3$-$C_8$-cycloalkyl in which optionally one methylene group is replaced by oxygen or sulphur or represents optionally halogen-, $C_1$-$C_4$-alkyl-, $C_1$-$C_4$-alkoxy-, $C_1$-$C_2$-haloalkyl-, $C_1$-$C_2$-haloalkoxy-, cyano- or nitro-substituted phenyl, or $Q^3$ and $Q^4$ together with the carbon atom to which they are attached preferably represent an optionally $C_1$-$C_4$-alkyl-, $C_1$-$C_4$-alkoxy- or $C_1$-$C_2$-haloalkyl-substituted $C_3$-$C_7$-ring in which optionally one ring atom is replaced by oxygen or sulphur.

G preferably represents hydrogen (a) or represents one of the groups

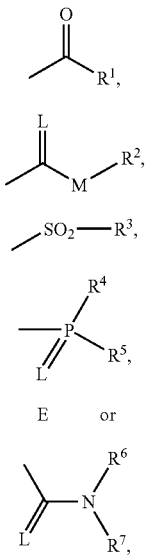

in particular (a), (b), (c) or (g), in which
E represents a metal ion equivalent or an ammonium ion,
L represents oxygen or sulphur, and
M represents oxygen or sulphur.

$R^1$ preferably represents in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, poly-$C_1$-$C_8$-alkoxy-$C_1$-$C_8$-alkyl or optionally halogen-, $C_1$-$C_6$-alkyl- or $C_1$-$C_6$-alkoxy-substituted $C_3$-$C_8$-cycloalkyl, in which optionally one or more (preferably not more than two) not directly adjacent ring members are replaced by oxygen and/or sulphur, represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl-substituted phenyl, represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl, represents optionally halogen- or $C_1$-$C_6$-alkyl-substituted 5- or 6-membered hetaryl (for example pyrazolyl, thiazolyl, pyridyl, pyrimidyl, furanyl or thienyl), represents optionally halogen- or $C_1$-$C_6$-alkyl-substituted phenoxy-$C_1$-$C_6$-alkyl or represents optionally halogen-, amino- or $C_1$-$C_6$-alkyl-substituted 5- or 6-membered hetaryloxy-$C_1$-$C_6$-alkyl (for example pyridyloxy-$C_1$-$C_6$-alkyl, pyrimidyloxy-$C_1$-$C_6$-alkyl or thiazolyloxy-$C_1$-$C_6$-alkyl).

$R^2$ preferably represents in each case optionally halogen-substituted $C_1$-$C_{20}$-alkyl, $C_2$-$C_{20}$alkenyl, $C_1$-$C_8$-alkoxy-$C_2$-$C_{18}$-alkyl, poly-$C_1$-$C_8$-alkoxy-$C_2$-$C_8$-alkyl, represents optionally halogen-, $C_1$-$C_6$-alkyl- or $C_1$-$C_6$-alkoxy-substituted $C_3$-$C_8$-cycloalkyl or represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl.

$R^3$ preferably represents optionally halogen-substituted $C_1$-$C_8$-alkyl or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl.

$R^4$ and $R^5$ independently of one another preferably represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio, $C_2$-$C_8$-alkenylthio, $C_3$-$C_7$-cycloalkylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio.

$R^6$ and $R^7$ independently of one another preferably represent hydrogen, represent in each case optionally halogen-substituted $C_1$-$C_8$-alkyl, $C_3$-$C_8$-cycloalkyl, $C_1$-$C_8$-alkoxy, $C_3$-$C_8$-alkenyl, $C_1$-$C_8$-alkoxy-$C_1$-$C_8$-alkyl, represent optionally halogen-, $C_1$-$C_8$-haloalkyl-, $C_1$-$C_8$-alkyl- or $C_1$-$C_8$-alkoxy-substituted phenyl, optionally halogen-, $C_1$-$C_8$-alkyl-, $C_1$-$C_8$-haloalkyl- or $C_1$-$C_8$-alkoxy-substituted benzyl or together represent an optionally $C_1$-$C_4$-alkyl-substituted $C_3$-$C_6$-alkylene radical in which optionally one carbon atom is replaced by oxygen or sulphur.

In the radical definitions mentioned as being preferred, halogen represents fluorine, chlorine, bromine and iodine, in particular fluorine, chlorine and bromine.

X particularly preferably represents fluorine, chlorine, bromine, $C_1$-$C_4$-alkyl, $C_2$-$C_4$-alkenyl, $C_1$-$C_4$-alkoxy, trifluoromethyl, trifluoromethoxy, trifluoroethoxy or cyano.

Z particularly preferably represents hydrogen, $C_2$-$C_4$-alkenyl, $C_2$-$C_4$-alkinyl or represents the radical

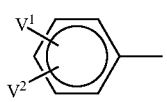

$V^1$ particularly preferably represents hydrogen, fluorine, chlorine, bromine, $C_1$-$C_6$-alkyl, $C_1$-$C_4$-alkoxy, $C_1$-$C_2$-haloalkyl, $C_1$-$C_2$-haloalkoxy, nitro or cyano.

$V^2$ particularly preferably represents hydrogen, fluorine, chlorine, bromine, $C_1$-$C_4$-alkyl, $C_1$-$C_4$-alkoxy, $C_1$-$C_2$-haloalkyl or $C_1$-$C_2$-haloalkoxy.

W and Y independently of one another particularly preferably represent hydrogen, fluorine, chlorine, bromine, $C_1$-$C_4$-alkyl, $C_1$-$C_4$-haloalkyl, $C_1$-$C_4$-alkoxy or $C_1$-$C_4$-haloalkoxy, with the proviso that, if Y represents 4-methyl, W and X do not simultaneously represent ethyl or W does not represent methoxy or difluoromethoxy if X represents ethyl and with the proviso that X does not represent alkenyl if Z does not represent hydrogen, CKE particularly preferably represents one of the groups

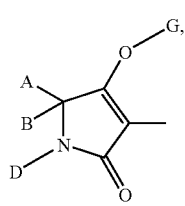
(1)

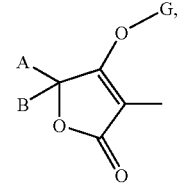
(2)

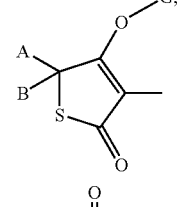
(3)

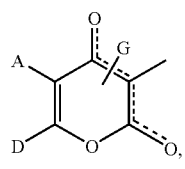
(4)

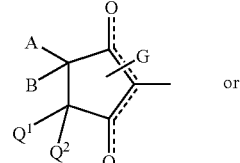
(5)

or

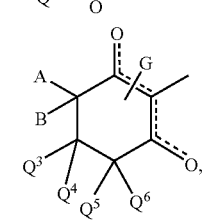
(6)

A particularly preferably represents hydrogen, in each case optionally fluorine—or chlorine—substituted $C_1$-$C_6$-alkyl, $C_1$-$C_4$-alkoxy-$C_1$-$C_4$-alkyl or optionally fluorine-, chlorine-, $C_1$-$C_4$-alkyl- or $C_1$-$C_4$-alkoxy-substituted $C_3$-$C_7$-cycloalkyl.

B particularly preferably represents hydrogen or $C_1$-$C_6$-alkyl, or

A, B and the carbon atom to which they are attached particularly preferably represent saturated $C_3$-$C_7$-cycloalkyl or unsaturated $C_5$-$C_7$-cycloalkyl in which optionally one ring member is replaced by oxygen or sulphur and which is optionally monosubstituted by $C_1$-$C_6$-alkyl, $C_1$-$C_3$-haloalkyl or $C_1$-$C_6$-alkoxy, or A, B and the carbon atom to which they are attached particularly preferably represent $C_5$-$C_6$-cycloalkyl which is substituted by an alkylenediyl or by an alkylenedioxy or by an alkylenedithiol group which, together with the carbon atom to which it is attached, forms a further five- or six-membered ring and which is optionally substituted by methyl or ethyl and optionally contains one or two not directly adjacent oxygen or sulphur atoms, or A, B and the carbon atom to which they are attached particularly preferably represent $C_3$-$C_6$-cycloalkyl or $C_5$-$C_6$-cycloalkenyl in which two substituents together with the carbon atoms to which they are attached represent in each case optionally $C_1$-$C_5$-alkyl-, $C_1$-$C_5$-alkoxy-, fluorine-, chlorine- or bromine-substituted $C_2$-$C_4$-alkanediyl, $C_2$-$C_4$-alkenediyl in which optionally one methylene group is replaced by oxygen or sulphur or represent butadienediyl.

D particularly preferably represents hydrogen, represents in each case optionally fluorine- or chlorine-substituted $C_1$-$C_6$-alkyl, $C_3$-$C_6$-alkenyl, $C_1$-$C_4$-alkoxy-$C_2$-$C_3$-alkyl, represents optionally $C_1$-$C_4$-alkyl-, $C_1$-$C_4$-alkoxy- or $C_1$-$C_2$-haloalkyl-substituted $C_3$-$C_7$-cycloalkyl in which optionally one methylene group is replaced by oxygen or sulphur or (but not in the case of compounds of the formula (I-1)) represents in each case optionally fluorine-, chlorine-, bromine-, $C_1$-$C_4$-alkyl-, $C_1$-$C_4$-haloalkyl-, $C_1$-$C_4$-alkoxy- or $C_1$-$C_4$-haloalkoxy-substituted phenyl, pyridyl or benzyl, or A and D together particularly preferably represent optionally substituted $C_3$-$C_5$-alkanediyl in which one methylene group may be replaced by oxygen or sulphur, possible substituents being $C_1$-$C_4$-alkyl, or A and D (in the case of the compounds of the formula (I-1)) together with the atoms to which they are attached represent one of the groups AD-1 to AD-10:

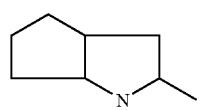
AD-1

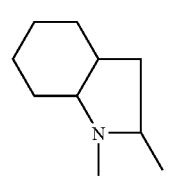
AD-2

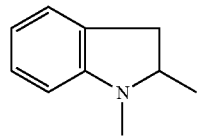
AD-3

AD-4

AD-5

AD-6

AD-7

AD-8

AD-9

AD-10

A and Q¹ together particularly preferably represent C₃-C₄-alkanediyl or C₃-C₄-alkenediyl, each of which is optionally mono- or disubstituted by identical or different substituents from the group consisting of C₁-C₄-alkyl and C₁-C₄-alkoxy, or Q¹ particularly preferably represents hydrogen.

Q² particularly preferably represents hydrogen.

Q⁴, Q⁵ and Q⁶ independently of one another particularly preferably represent hydrogen or C₁-C₂-alkyl.

Q³ particularly preferably represents hydrogen, C₁-C₄-alkyl, C₁-C₄-alkoxy-C₁-C₂-alkyl, C₁-C₄-alkylthio-C₁-C₂-alkyl or optionally methyl- or methoxy-substituted C₃-C₆-cycloalkyl in which optionally one methylene group is replaced by oxygen or sulphur, or Q³ and Q⁴ together with the carbon to which they are attached particularly preferably represent an optionally C₁-C₄-alkyl- or C₁-C₄-alkoxy-substituted saturated C₅-C₆-ring in which optionally one ring member is replaced by oxygen or sulphur.

G particularly preferably represents hydrogen (a) or represents one of the groups (b)
$\underset{R^1}{\overset{O}{\|}}$, (c)
$\underset{M}{\overset{L}{\|}}\text{—}R^2$, (d)
$\text{—SO}_2\text{—}R^3$, (e)
$\underset{L}{\overset{R^4}{\|}}\text{P}\underset{}{\overset{}{\text{—}R^5}}$, (f)
E or (g)
$\underset{L}{\overset{R^6}{\|}}\text{—N}\underset{}{\overset{}{R^7}}$, in particular (a), (b) or (c),
in which
E represents a metal ion equivalent or an ammonium ion,
L represents oxygen or sulphur,
M represents oxygen or sulphur,
R¹ particularly preferably represents in each case optionally fluorine- or chlorine-substituted C₁-C₁₆-alkyl, C₂-C₆₁-alkenyl, C₁-C₆-alkoxy-C₁-C₄-alkyl, C₁-C₆-alkylthio-C₁-C₆-alkyl or optionally fluorine-, chlorine-, C₁-C₄-alkyl- or C₁-C₄-alkoxy-substituted C₃-C₇-cycloalkyl in which optionally one or two not directly adjacent ring members are replaced by oxygen and/or sulphur,
represents optionally fluorine-, chlorine-, bromine-, cyano-, nitro-, C₁-C₄-alkyl-, C₁-C₄-alkoxy-, C₁-C₃-haloalkyl- or C₁-C₃-haloalkoxy-substituted phenyl,
R² particularly preferably represents in each case optionally fluorine-substituted C₁-C₁₆-alkyl, C₂-C₁₆-alkenyl or C₁-C₆-alkoxy-C₂-C₆-alkyl,
represents optionally fluorine-, chlorine-, C₁-C₄-alkyl- or C₁-C₄-alkoxy-substituted C₃-C₇-cycloalkyl,
represents in each case optionally fluorine-, chlorine-, bromine-, cyano-, nitro-, C₁-C₄-alkyl-, C₁-C₃-alkoxy-, C₁-C₃-haloalkyl- or C₁-C₃-haloalkoxy-substituted phenyl or benzyl.
R³ particularly preferably represents optionally fluorine-substituted C₁-C₆-alkyl or represents optionally fluorine-, chlorine-, bromine-, C₁-C₄-alkyl-, C₁-C₄-alkoxy-, C₁-C₃-haloalkyl-, C₁-C₃-haloalkoxy-, cyano- or nitro-substituted phenyl.
R⁴ particularly preferably represents C₁-C₆-alkyl, C₁-C₆-alkoxy, C₁-C₆-alkylamino, di-(C₁-C₆-alkyl)amino, C₁-C₆-alkylthio, C₃-C₄-alkenylthio, C₃-C₆-cycloalkylthio or represents in each case optionally fluorine-, chlorine-, bromine-, nitro-, cyano-, C₁-C₃-alkoxy-, C₁-C₃-haloalkoxy-, C₁-C₃-alkylthio-, C₁-C₃-haloalkylthio-, C₁-C₃-alkyl- or C₁-C₃-haloalkyl-substituted phenyl, phenoxy or phenylthio.
R⁵ particularly preferably represents C₁-C₆-alkoxy or C₁-C₆-alkylthio.
R⁶ particularly preferably represents hydrogen, C₁-C₆-alkyl, C₃-C₆-cycloalkyl, C₁-C₆-alkoxy; C₃-C₆-alkenyl, C₁-C₆-alkoxy-C₁-C₄-alkyl, represents optionally fluorine-, chlorine-, bromine-, $C_1$-$C_3$-haloalkyl-, $C_1$-$C_4$-alkyl- or $C_1$-$C_4$-alkoxy-substituted phenyl, represents optionally fluorine-, chlorine-, bromine-, $C_1$-$C_4$-alkyl-, $C_1$-$C_3$-haloalkyl- or $C_1$-$C_4$-alkoxy-substituted benzyl.

$R^7$ particularly preferably represents $C_1$-$C_6$-alkyl, $C_3$-$C_6$-alkenyl or $C_1$-$C_6$-alkoxy-$C_1$-$C_4$-alkyl.

$R^6$ and $R^7$ together particularly preferably represent an optionally methyl- or ethyl-substituted $C_4$-$C_5$-alkylene radical in which optionally one methylene group is replaced by oxygen or sulphur.

In the radical definitions mentioned as being particularly preferred, halogen represents fluorine, chlorine, bromine and iodine, in particular fluorine, chlorine and bromine.

X very particularly preferably represents chlorine, bromine, methyl, ethyl, propyl, vinyl, methoxy, ethoxy, trifluoromethyl, difluoromethoxy, trifluoro-methoxy or cyano.

Z very particularly preferably represents hydrogen, vinyl, ethinyl or represents the radical

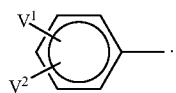

$V^1$ very particularly preferably represents hydrogen, fluorine, chlorine, bromine, methyl, ethyl, n-propyl, isopropyl, n-butyl, isobutyl, tert-butyl, methoxy, ethoxy, n-propoxy, isopropoxy, trifluoromethyl, trifluoromethoxy, or cyano.

$V^2$ very particularly preferably represents hydrogen, fluorine, chlorine, methyl, ethyl, n-propyl, isopropyl, methoxy, ethoxy, trifluoromethyl or trifluoro-methoxy.

W and Y independently of one another very particularly preferably represent hydrogen, fluorine, chlorine, bromine, methyl, ethyl, n-propyl, methoxy or ethoxy, with the proviso that, if Y represents 4-methyl, W and X do not simultaneously represent ethyl or W does not represent methoxy or difluoromethoxy if X represents ethyl and with the proviso that X does not represent vinyl if Z does not represent hydrogen.

CKE very particularly preferably represents one of the groups (1)

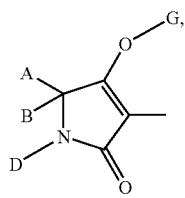

(2)

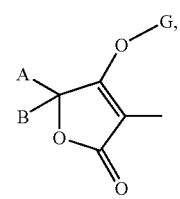

(3)

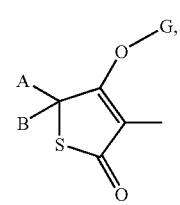

-continued (4)

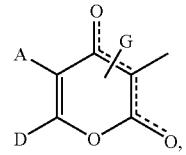

(5)

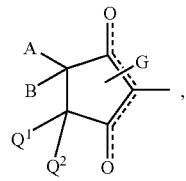

(6)

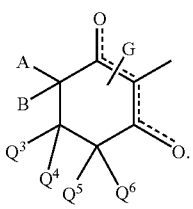

A very particularly preferably represents hydrogen, represents $C_1$-$C_4$-alkyl or $C_1$-$C_2$-alkoxy-$C_1$-$C_2$-alkyl, each of which is optionally mono- to tri-substituted by fluorine, or represents $C_3$-$C_6$-cycloalkyl which is optionally monosubstituted by fluorine, methyl, ethyl or methoxy.

B very particularly preferably represents hydrogen, methyl or ethyl, or

A, B and the carbon atom to which they are attached very particularly preferably represent saturated $C_5$-$C_6$-cycloalkyl in which optionally one ring member is replaced by oxygen or sulphur and which is optionally monosubstituted by methyl, ethyl, propyl, isopropyl, trifluoromethyl, methoxy, ethoxy, propoxy, butoxy or isobutoxy, or A, B and the carbon atom to which they are attached very particularly preferably represent $C_5$-$C_6$-cycloalkyl which is substituted by an alkylenedioxyl group which contains two not directly adjacent oxygen atoms, D very particularly preferably represents hydrogen, represents in each case optionally fluorine- or chlorine-substituted $C_1$-$C_4$-alkyl, $C_3$-$C_4$-alkenyl, $C_1$-$C_2$-alkoxy-$C_2$-$C_3$-alkyl or $C_3$-$C_6$-cycloalkyl in which optionally one methylene group is replaced by oxygen or sulphur, or (but not in the case of the compounds of the formula (I-1)) represents phenyl or pyridyl, each of which is optionally monosubstituted by fluorine, chlorine, bromine, methyl, ethyl, n-propyl, isopropyl, methoxy, ethoxy, trifluoromethyl or trifluoromethoxy, or A and D together very particularly preferably represent optionally substituted $C_3$-$C_4$-alkanediyl in which optionally one carbon atom is replaced by oxygen or sulphur and which is optionally substituted by methyl, or A and D (in the case of compounds of the formula (I-1)) together with the atom to which they are attached represent the group

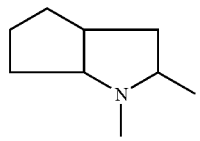 AD-1

- A and $Q^1$ together very particularly preferably represent $C_3$-$C_4$-alkanediyl which is optionally mono- or disubstituted by methyl or methoxy, or
- $Q^1$ very particularly preferably represents hydrogen.
- $Q^2$ very particularly preferably represents hydrogen.
- $Q^4$, $Q^5$ and $Q^6$ independently of one another very particularly preferably represent hydrogen or methyl.
- $Q^3$ very particularly preferably represents hydrogen, methyl, ethyl or $C_3$-$C_6$-cycloalkyl, or
- $Q^3$ and $Q^4$ together with the carbon to which they are attached very particularly preferably represent an optionally methyl- or methoxy-substituted saturated $C_5$-$C_6$-ring in which optionally one ring member is replaced by oxygen or sulphur.
- G very particularly preferably represents hydrogen (a) or represents one of the groups

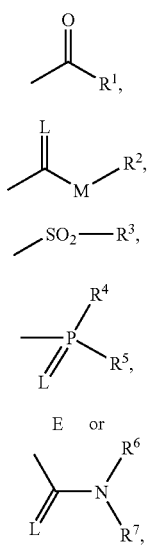

in particular (a), (b) or (c),
in which
E represents a metal ion equivalent or an ammonium ion,
L represents oxygen,
M represents oxygen or sulphur.
$R^1$ very particularly preferably represents $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl each of which is optionally mono- to trisubstituted by fluorine or chlorine, or represents $C_3$-$C_6$-cycloalkyl which is optionally mono- or disubstituted by fluorine, chlorine, methyl, ethyl or methoxy,
represents phenyl which is optionally mono- or disubstituted by fluorine, chlorine, bromine, cyano, nitro, methyl, methoxy, trifluoromethyl or trifluoromethoxy, $R^2$ very particularly preferably represents $C_1$-$C_{10}$-alkyl, $C_2$-$C_{10}$-alkenyl or $C_1$-$C_4$-alkoxy-$C_2$-$C_4$-alkyl, each of which is optionally mono- to trisubstituted by fluorine, or represents $C_3$-$C_6$-cycloalkyl which is optionally monosubstituted by fluorine, methyl or methoxy,
or represents phenyl or benzyl, each of which is optionally mono- or disubstituted by fluorine, chlorine, cyano, nitro, methyl, methoxy, trifluoromethyl or trifluoromethoxy.

$R^3$ very particularly preferably represents methyl, ethyl, n-propyl, isopropyl, each of which is optionally mono- to trisubstituted by fluorine, or represents phenyl which, is optionally monosubstituted by fluorine, chlorine, bromine, methyl, tert-butyl, methoxy, trifluoromethyl, trifluoromethoxy, cyano or nitro.

$R^4$ very particularly preferably represents $C_1$-$C_4$-alkyl, $C_1$-$C_4$-alkoxy, $C_1$-$C_4$-alkylamino, di-($C_1$-$C_4$-alkyl)amino, $C_1$-$C_4$-alkylthio or represents phenyl, phenoxy or phenylthio, each of which is optionally monosubstituted by fluorine, chlorine, bromine, nitro, cyano, $C_1$-$C_2$-alkoxy, $C_1$-$C_2$-fluoroalkoxy, $C_1$-$C_2$-alkylthio, $C_1$-$C_2$-fluoroalkylthio or $C_1$-$C_3$-alkyl.

$R^5$ very particularly preferably represents $C_1$-$C_3$-alkoxy or $C_1$-$C_3$-alkylthio.

$R^6$ very particularly preferably represents hydrogen, represents $C_1$-$C_4$-alkyl, $C_3$-$C_6$-cycloalkyl, $C_1$-$C_4$-alkoxy, $C_3$-$C_4$-alkenyl, $C_1$-$C_4$-alkoxy-$C_1$-$C_4$-alkyl, represents phenyl which is optionally mono- or disubstituted by fluorine, chlorine, bromine, trifluoromethyl, methyl or methoxy, represents benzyl which is optionally monosubstituted by fluorine, chlorine, bromine, methyl, trifluoromethyl or methoxy.

$R^7$ very particularly preferably represents $C_1$-$C_4$-alkyl, $C_3$-$C_4$-alkenyl or $C_1$-$C_4$-alkoxy-$C_1$-$C_2$-alkyl.

$R^6$ and $R^7$ together very particularly preferably represent a $C_5$-$C_6$-alkylene radical in which optionally one methylene group is replaced by oxygen or sulphur.

Most preferred are compounds in which Z represents hydrogen and Y is located in the position para to the group CKE or in which Z represents the group

in the position para or meta to the group CKE.

Emphasis is given to compounds in which Y represents 4-alkyl (in particular 4-methyl).

The general or preferred radical definitions or illustrations given above can be combined with one another as desired, i.e. including combinations between the respective ranges and preferred ranges.

Preference according to the invention is given to the compounds of the formula (I) which contain a combination of the meanings given above as being preferred (preferable).

Particular preference according to the invention is given to the compounds of the formula (I) which contain a combination of the meanings given above as being particularly preferred.

Very particular preference according to the invention is given to the compounds of the formula (I) which contain a combination of the meanings given above as being very particularly preferred.

Saturated or unsaturated hydrocarbon radicals such as alkyl or alkenyl can, as far as this is possible, in each case be straight-chain or branched, including in combination with heteroatoms, such as, for example, in alkoxy.

Unless indicated otherwise, optionally substituted radicals can be mono- or polysubstituted, where in the case of polysubstitution the substituents can be identical or different.

In the following, additional preferred radical definitions in the aryl moiety of the compounds of the formula (I) are mentioned. Compounds of the formula (I) containing these radical definitions form preferred subgroups of the compounds of the formula (I).

The following applies for such subgroups:

W preferably represents $C_1$-$C_6$-alkyl or $C_1$-$C_6$-alkoxy,

X preferably represents halogen, $C_1$-$C_6$-alkyl, $C_1$-$C_6$-alkoxy, $C_1$-$C_4$-halogenoalkyl, $C_1$-$C_4$-halogenoalkoxy or cyano, Y is preferably in the 4-position where it preferably represents hydrogen, halogen, cyano or $C_1$-$C_4$-halogenoalkyl and Z preferably represents hydrogen.

W also preferably represents hydrogen, halogen or $C_1$-$C_6$-alkyl,

X also preferably represents halogen, $C_1$-$C_6$-alkyl, $C_1$-$C_6$-alkoxy, $C_1$-$C_4$-halogenoalkyl, $C_1$-$C_4$-halogenoalkoxy or cyano, Y is also preferably in the 4-position where it preferably represents the radical

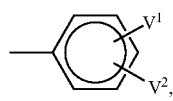

Z preferably also represents hydrogen, $V^1$ preferably also represents halogen, $C_1$-$C_{12}$-alkyl, $C_1$-$C_6$-alkoxy, $C_1$-$C_4$-halogenoalkyl or $C_1$-$C_4$-halogenoalkoxy, $V^2$ also preferably represents hydrogen, halogen, $C_1$-$C_6$-alkyl, $C_1$-$C_6$-alkoxy or $C_1$-$C_4$-halogenoalkyl, $V^1$ and $V^2$ also together preferably represent $C_3$-$C_4$-alkanediyl, which can optionally be substituted by halogen and/or $C_1$-$C_2$-allyl and which can optionally be interrupted by one or two oxygen atoms.

W also preferably represents hydrogen or $C_1$-$C_6$-alkyl,

X also preferably represents halogen, $C_1$-$C_6$-alkyl, $C_1$-$C_6$-alkoxy, $C_1$-$C_4$-halogenoalkyl, $C_1$-$C_4$-halogenoalkoxy or cyano or Y is also preferably in the 5-position where it preferably represents the radical

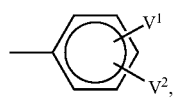

Z is also preferably in the 4-position where it preferably represents hydrogen, $C_1$-$C_6$-alkyl or halogen, $V^1$ also preferably represents halogen, $C_1$-$C_{12}$-alkyl, $C_1$-$C_6$-alkoxy, $C_1$-$C_4$-halogenoalkyl or $C_1$-$C_4$-halogenoalkoxy, $V^2$ also preferably represents hydrogen, halogen, $C_1$-$C_6$-alkyl, $C_1$-$C_6$-alkoxy or $C_1$-$C_4$-halogenoalkyl, $V^1$ and $V^2$ together also preferably represent $C_3$-$C_4$-alkanediyl, which can optionally be substituted by halogen and $C_1$-$C_2$-alkyl and which can optionally be interrupted by one or two oxygen atoms.

W also preferably represents hydrogen, methyl, propyl, isopropyl or halogen,

X also preferably represents halogen, $C_1$-$C_6$-alkyl, $C_1$-$C_6$-alkoxy, $C_1$-$C_4$-halogenoalkyl, $C_1$-$C_4$-halogenoalkoxy or cyano, Y is also preferably in the 3- or 5-position where it preferably represents hydrogen, halogen or $C_1$-$C_6$-alkyl, Z is also preferably in the 4-position where it preferably represents hydrogen, halogen, $C_1$-alkyl, $C_1$-$C_4$-halogenoalkyl, cyano or $C_1$-$C_4$-halogenoalkoxy.

The following also applies for the subgroups:

W particularly preferably represents $C_1$-$C_4$-alkyl or $C_1$-$C_4$-alkoxy,

X particularly preferably represents chlorine, bromine, $C_1$-$C_4$-alkyl, $C_1$-$C_4$-alkoxy, $C_1$-$C_2$-halogenoalkyl, $C_1$-$C_2$-halogenoalkoxy or cyano, Y is particularly preferably in the 4-position where it particularly preferably represents hydrogen, chlorine, bromine, cyano or trifluoromethyl.

Z particularly preferably represents hydrogen.

W also particularly preferably represents hydrogen, chlorine, bromine or $C_1$-$C_4$-alkyl, X also particularly preferably represents chlorine, bromine, $C_1$-$C_4$-alkyl, $C_1$-$C_4$-alkoxy, $C_1$-$C_2$-halogenoalkyl, $C_1$-$C_2$-halogenoalkoxy or cyano, Y is also particularly preferably in the 4-position where it particularly preferably represents the radical

Z also particularly preferably represents hydrogen, $V^1$ also particularly preferably represents fluorine, chlorine, $C_1$-$C_4$-alkyl, $C_1$-$C_4$-alkoxy, $C_1$-$C_2$-halogenoalkyl or $C_1$-$C_2$-halogenoalkoxy, $V^2$ also particularly preferably represents hydrogen, fluorine, chlorine, $C_1$-$C_4$-alkyl, $C_1$-$C_4$-alkoxy or $C_1$-$C_2$-halogenoalkyl, $V^1$ and $V^2$ together also particularly preferably represent —O—CH$_2$—O— and —O—CF$_2$—O—.

W also particularly preferably represents hydrogen or $C_1$-$C_4$-alkyl,

X also particularly preferably represents chlorine, $C_1$-$C_4$-alkyl or $C_1$-$C_2$-halogenoalkyl, Y is also particularly preferably in the 5-position where it particularly preferably represents the radical

Z is also particularly preferably in the 4-position where it particularly preferably represents hydrogen, $C_1$-$C_4$-alkyl or chlorine.

$V^1$ also particularly preferably represents fluorine, chlorine, $C_1$-$C_4$-alkyl, $C_1$-$C_4$-alkoxy, $C_1$-$C_2$-halogenoalkyl or $C_1$-$C_2$-halogenoalkoxy, $V^2$ also particularly preferably represents hydrogen, fluorine, chlorine, $C_1$-$C_4$-alkyl, $C_1$-$C_4$-alkoxy or $C_1$-$C_2$-halogenoalkyl, $V^1$ and $V^2$ together also particularly preferably represent —O—CH$_2$—O— and —O—CF$_2$—O—.

W also particularly preferably represents hydrogen, methyl, chlorine or bromine, X also particularly preferably represents chlorine, bromine, $C_1$-$C_4$-alkyl, $C_1$-$C_4$-alkoxy, $C_1$-$C_2$-halogenoalkyl, $C_1$-$C_2$-halogenoalkoxy or cyano, Y is also particularly preferably in the 3- or 5-position where it particularly preferably represents hydrogen, chlorine, bromine or $C_1$-$C_4$-alkyl, Z is also preferably in the 4-position where it preferably represents hydrogen, chlorine, bromine, $C_1$-$C_4$-alkyl, $C_1$-$C_2$-halogenoalkyl, cyano or $C_1$-$C_2$-halogenoalkoxy.

The following also applies for the subgroups:

W very particularly preferably represents ethyl or methoxy,

X very particularly preferably represents chlorine, bromine, methyl, ethyl, propyl, methoxy, trifluoromethyl, difluoromethoxy, trifluoroethoxy or cyano, Y is very particularly preferably in the 4-position where it very particularly preferably represents hydrogen, chlorine or bromine, Z very particularly preferably represents hydrogen.

W also particularly preferably represents hydrogen, chlorine, bromine or methyl, X also very particularly preferably represents chlorine, bromine, methyl, ethyl, propyl, methoxy, trifluoromethyl, difluoromethoxy or cyano, Y is also very particularly preferably in the 4-position where it very particularly preferably represents the radical

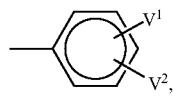

Z also very particularly preferably represents hydrogen, $V^1$ also very particularly preferably represents fluorine, chlorine, methyl, methoxy, trifluoromethyl or trifluoromethoxy, $V^2$ also very particularly preferably represents hydrogen, fluorine, chlorine, methyl, methoxy or trifluoromethyl.

W also very particularly preferably represents hydrogen or methyl,

X also very particularly preferably represents chlorine, methyl or trifluoromethyl, Y is also very particularly preferably in the 5-position where it very particularly preferably represents the radical

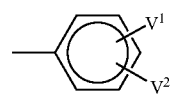

Z is also very particularly preferably in the 4-position where it very particularly preferably represents hydrogen or methyl, $V^1$ also very particularly preferably represents fluorine, chlorine, methyl, methoxy, trifluoromethyl or trifluoromethoxy, $V^2$ also very particularly preferably represents hydrogen, fluorine, chlorine, methyl, methoxy or trifluoromethyl.

W also very particularly preferably represents hydrogen, methyl, chlorine or bromine, X also very particularly preferably represents chlorine, bromine, methyl, methoxy, trifluoromethyl, difluoromethoxy, trifluoroethoxy or cyano, Y is also very particularly preferably in the 3- or 5-position where it very particularly preferably represents hydrogen, chlorine, bromine or methyl, Z is also very particularly preferably in the 4-position where it very particularly preferably represents hydrogen, chlorine, bromine, methyl, trifluoromethyl or trifluoromethoxy.

The following also applies for the subgroups:

W particularly preferably represents ethyl or methoxy,

X particularly preferably represents chlorine, bromine, methyl, ethyl, propyl, methoxy, trifluoromethyl, difluoromethoxy or cyano, Y is particularly preferably in the 4-position where it particularly preferably represents hydrogen, chlorine or bromine, Z is particularly preferably in the 5-position where it particularly preferably represents hydrogen.

The following also applies for the subgroups:

W also particularly preferably represents hydrogen, chlorine, bromine or methyl, X also particularly preferably represents chlorine, bromine, methyl, ethyl, propyl, methoxy, trifluoromethyl, difluoromethoxy or cyano, Y is also particularly preferably in the 4-position where it particularly preferably represents the radical

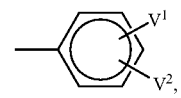

Z also particularly preferably represents hydrogen, $V^1$ also particularly preferably represents fluorine, chlorine, methyl, methoxy, trifluoromethyl or trifluoromethoxy, $V^2$ also particularly preferably represents hydrogen, fluorine, chlorine, methyl, methoxy or trifluoromethyl.

W also particularly represents hydrogen or methyl,

X also particularly preferably represents chlorine or methyl,

Y is also particularly preferably in the 5-position where it particularly preferably represents the radical

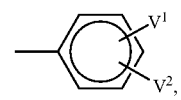

Z is also particularly preferably in the 4-position where it particularly preferably represents hydrogen or methyl, $V^1$ also particularly preferably represents fluorine, chlorine, methyl, methoxy, trifluoromethyl or trifluoromethoxy, $V^2$ also particularly preferably represents hydrogen, fluorine, chlorine, methyl, methoxy or trifluoromethyl.

The following also applies for the subgroups:

W also particularly preferably represents hydrogen, methyl, chlorine or bromine, X also particularly preferably represents chlorine, bromine, methyl, methoxy, trifluoromethyl, difluoromethoxy or cyano, Y is also particularly preferably in the 3- or 5-position where it particularly preferably represents hydrogen, chlorine, bromine or methyl, Z is also particularly preferably in the 4-position where it particularly preferably represents hydrogen, chlorine, bromine, methyl, trifluoromethyl or trifluoromethoxy.

In addition to the compounds mentioned in the examples, the following compounds of the formula (I-1-a) may be specifically mentioned:

TABLE 1

[Structure: pyrrolinone with OH, A, B, N-D, W, X, Y, Z substituents on phenyl ring]

W=CH$_3$, X=CH$_3$, Y=4-CH$_3$, Z=H.

| A | B | D |
|---|---|---|
| CH$_3$ | CH$_3$ | H |
| C$_2$H$_5$ | CH$_3$ | H |
| C$_3$H$_7$ | CH$_3$ | H |
| i-C$_3$H$_7$ | CH$_3$ | H |
| △ (cyclopropyl) | CH$_3$ | H |
|  | —(CH$_2$)$_4$— | H |
|  | —(CH$_2$)$_5$— | H |
|  | —(CH$_2$)$_2$—O—(CH$_2$)$_2$— | H |
|  | —CH$_2$—O—(CH$_2$)$_3$— | H |
|  | —CH$_2$—CHCH$_3$—(CH$_2$)$_3$— | H |
|  | —(CH$_2$)$_2$—CHCH$_3$—(CH$_2$)$_2$— | H |
|  | —(CH$_2$)$_2$—CHOCH$_3$—(CH$_2$)$_2$— | H |
|  | —(CH$_2$)$_2$—CHOC$_2$H$_5$—(CH$_2$)$_2$— | H |
|  | —(CH$_2$)$_2$—C(CH$_3$)$_2$—(CH$_2$)$_2$— | H |
|  | —(CH$_2$)$_3$— | H |
|  | —(CH$_2$)$_4$— | H |
|  | —(CH$_2$)$_2$—O—(CH$_2$)— | H |
|  | —(CH$_2$)$_2$—S—CH$_2$— | H |
|  | —CH$_2$—CH———CH— with —(CH$_2$)$_3$— bridge | H |
| H | CH$_3$ | H |
| H | C$_2$H$_5$ | H |
| H | C$_3$H$_7$ | H |
| H | i-C$_3$H$_7$ | H |
| H | △ (cyclopropyl) | H |
| H | (cyclopentyl) | H |
| CH$_3$ | CH$_3$ | H |
| CH$_3$ | C$_2$H$_5$ | H |
| CH$_3$ | i-C$_3$H$_7$ | H |
| CH$_3$ | △ (cyclopropyl) | H |

Table 2: A, B and D are as indicated in Table 1
W=CH$_3$; X=CH$_3$; Y=4-Cl; Z=H.
Table 3: A, B and D are as indicated in Table 1
W=CH$_3$; X=CH$_3$; Y=4-Br; Z=H.
Table 4: A, B and D are as indicated in Table 1
W=C$_2$H$_5$; X=CH$_3$; Y=4-Cl; Z=H.
Table 5: A, B and D are as indicated in Table 1
W=C$_2$H$_5$; X=CH$_3$; Y=4-Br; Z=H.
Table 6: A, B and D are as indicated in Table 1
W=C$_2$H$_5$; X=C$_2$H$_5$; Y=4-Cl; Z=H.
Table 7: A, B and D are as indicated in Table 1
W=C$_2$H$_5$; X=C$_2$H$_5$; Y=4-Br; Z=H.
Table 8: A, B and D are as indicated in Table 1
W=CH$_3$; X=Cl; Y=4-Cl; Z=H.
Table 9: A, B and D are as indicated in Table 1
W=CH$_3$; X=Br; Y=4-Br; Z=H.
Table 10: A, B and D are as indicated in Table 1
W=CH$_3$; X=Cl; Y=4-Br; Z=H.
Table 11: A, B and D are as indicated in Table 1
W=CH$_3$; X=Br; Y=4-Cl; Z=H.
Table 12: A, B and D are as indicated in Table 1
W=C$_2$H$_5$; X=Cl; Y=4-Cl; Z=H.
Table 13: A, B and D are as indicated in Table 1
W=C$_2$H$_5$; X=Br; Y=4-Br; Z=H.
Table 14: A, B and D are as indicated in Table 1
W=C$_2$H$_5$; X=Cl; Y=4-Br; Z=H.
Table 15: A, B and D are as indicated in Table 1
W=C$_2$H$_5$; X=Br; Y=4-Cl; Z=H.
Table 16: A, B and D are as indicated in Table 1
W=CH$_3$; X=CH$_3$; Y=H; Z=4-(4-Cl—C$_6$H$_4$).
Table 17: A, B and D are as indicated in Table 1
W=CH$_3$; X=Cl; Y=H; Z=4-(4-Cl—C$_6$H$_4$).
Table 18: A, B and D are as indicated in Table 1
W=C$_2$H$_5$; X=CH$_3$; Y=H; Z=4-(4-Cl—C$_6$H$_4$).
Table 19: A, B and D are as indicated in Table 1
W=C$_2$H$_5$; X=Cl; Y=H; Z=4-(4-Cl—C$_6$H$_4$).
Table 20: A, B and D are as indicated in Table 1
W=C$_2$H$_5$; X=C$_2$H$_5$; Y=H; Z=4-(4-Cl—C$_6$H$_4$).
Table 21: A, B and D are as indicated in Table 1
W=H; X=CH$_3$; Y=H; Z=5-(4-Cl—C$_6$H$_4$).
Table 22: A, B and D are as indicated in Table 1
W=H; X=CH$_3$; Y=4-CH$_3$; Z=5-(4-Cl—C$_6$H$_4$).

In addition to the compounds mentioned in the Preparation Examples, the following compounds of the formula (I-2-a) may be specifically mentioned:

TABLE 23

[Structure: furanone with OH, A, B, O, W, X, Y, Z substituents on phenyl ring]

W=CH$_3$, X=CH$_3$, Y=4-CH$_3$, Z=H

| A | B |
|---|---|
| CH$_3$ | CH$_3$ |
| C$_2$H$_5$ | CH$_3$ |
| C$_3$H$_7$ | CH$_3$ |
| i-C$_3$H$_7$ | CH$_3$ |
|  | —(CH$_2$)$_5$— |
|  | —(CH$_2$)$_2$—O—(CH$_2$)$_2$— |
|  | —CH$_2$—O—(CH$_2$)$_3$— |
|  | —CH$_2$—CHCH$_3$—(CH$_2$)$_3$— |
|  | —(CH$_2$)$_2$—CHCH$_3$—(CH$_2$)$_2$— |
|  | —(CH$_2$)$_2$—CHOCH$_3$—(CH$_2$)$_2$— |
|  | —(CH$_2$)$_2$—CHOC$_2$H$_5$—(CH$_2$)$_2$— |

Table 24: A and B are as indicated in Table 23
W=CH$_3$; X=CH$_3$; Y=4-Cl; Z=H.
Table 25: A and B are as indicated in Table 23
W=CH$_3$; X=CH$_3$; Y=4-Br; Z=H.
Table 26: A and B are as indicated in Table 23
W=C$_2$H$_5$; X=CH$_3$; Y=4-Cl; Z=H.
Table 27: A and B are as indicated in Table 23
W=C$_2$H$_5$; X=CH$_3$; Y=4-Br; Z=H.
Table 28: A and B are as indicated in Table 23
W=C$_2$H$_5$; X=C$_2$H$_5$; Y=4-Cl; Z=H.

Table 29: A and B are as indicated in Table 23
W=C$_2$H$_5$; X=C$_2$H$_5$; Y=4-Br; Z=H.
Table 30: A and B are as indicated in Table 23
W=CH$_3$; X=CH$_3$; Y=H; Z=4-(4-Cl—C$_6$H$_4$).
Table 31: A and B are as indicated in Table 23
W=CH$_3$; X=C$_2$H$_5$; Y=H; Z=4-(4-Cl—C$_6$H$_4$).
Table 32: A and B are as indicated in Table 23
W=C$_2$H$_5$; X=C$_2$H$_5$; Y=H; Z=4-(4-Cl—C$_6$H$_4$).
Table 33: A and B are as indicated in Table 23
W=Cl; X=CH$_3$; Y=H; Z=4-(4-Cl—C$_6$H$_4$).
Table 34: A and B are as indicated in Table 23
W=Cl; X=C$_2$H$_5$; Y=H; Z=4-(4-Cl—C$_6$H$_4$).
Table 35: A and B are as indicated in Table 23
W=H; X=CH$_3$; Y=H; Z=5-(4-Cl—C$_6$H$_4$).
Table 36: A and B are as indicated in Table 23
W=H; X=CH$_3$; Y=4-CH$_3$; Z=5-(4-Cl—C$_6$H$_4$).

The combinations for W, X, Y and Z described in Tables 1-36 are likewise preferred combinations of radicals in the compounds of the formula (I).

Preferred meanings of the groups listed above in connection with the compounds improving crop plant compatibility ("herbicide safeners") of the formulae (Ia), (IIb), (IIc), (IId) and (IIe) are defined below.

n preferably represents the number 0, 1, 2, 3 or 4.

$A^1$ preferably represents one of the divalent heterocyclic groupings shown below

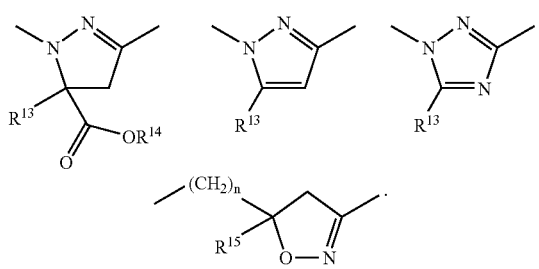

$A^2$ preferably represents in each case optionally methyl-, ethyl-, methoxycarbonyl- or ethoxy-carbonyl-substituted methylene or ethylene.

$R^8$ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^9$ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^{10}$ preferably represents in each case optionally fluorine-, chlorine- and/or bromine-substituted methyl, ethyl, n- or i-propyl.

$R^{11}$ preferably represents hydrogen, in each case optionally fluorine- and/or chlorine-substituted methyl, ethyl, n- or i-propyl, n-, i-, s- or t-butyl, propenyl, butenyl, propinyl or butinyl, methoxymethyl, ethoxymethyl, methoxyethyl, ethoxyethyl, dioxolanylmethyl, furyl, furylmethyl, thienyl, thiazolyl, piperidinyl, or optionally fluorine-, chlorine-, methyl-, ethyl-, n- or i-propyl-, n-, i-, s- or t-butyl-substituted phenyl.

$R^{12}$ preferably represents hydrogen, in each case optionally fluorine- and/or chlorine-substituted methyl, ethyl, n- or i-propyl, n-, i-, s- or t-butyl, propenyl, butenyl, propinyl or butinyl, methoxymethyl, ethoxymethyl, methoxyethyl, ethoxyethyl, dioxolanylmethyl, furyl, furylmethyl, thienyl, thiazolyl, piperidinyl, or optionally fluorine-, chlorine-, methyl-, ethyl-, n- or i-propyl-, n-, i-, s- or t-butyl-substituted phenyl, or together with $R^{11}$ represents one of the radicals —CH$_2$—O—CH$_2$—CH$_2$— and —CH$_2$—CH$_2$—O—CH$_2$—CH$_2$—, which are optionally substituted by methyl, ethyl, furyl, phenyl, a fused-on benzene ring or by two substituents which together with the C atom to which they are attached form a 5- or 6-membered carbocycle.

$R^{13}$ preferably represents hydrogen, cyano, fluorine, chlorine, bromine, or represents in each case optionally fluorine-, chlorine- and/or bromine-substituted methyl, ethyl, n- or i-propyl, cyclopropyl, cyclobutyl, cyclopentyl, cyclohexyl or phenyl.

$R^{14}$ preferably represents hydrogen, optionally hydroxyl-, cyano-, fluorine-, chlorine-, methoxy-, ethoxy-, n- or i-propoxy-substituted methyl, ethyl, n- or i-propyl, n-, i-, s- or t-butyl.

$R^{15}$ preferably represents hydrogen, cyano, fluorine, chlorine, bromine, or represents in each case optionally fluorine-, chlorine- and/or bromine-substituted methyl, ethyl, n- or i-propyl, n-, i-, s- or t-butyl, cyclopropyl, cyclobutyl, cyclopentyl, cyclohexyl or phenyl.

$X^1$ preferably represents nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^2$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^3$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$R^{16}$ preferably represents hydrogen, methyl, ethyl, n- or i-propyl.

$R^{17}$ preferably represents hydrogen, methyl, ethyl, n- or i-propyl.

$R^{18}$ preferably represents hydrogen, in each case optionally cyano-, fluorine-, chlorine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, or in each case: optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino.

$R^{19}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propinyl or butinyl, or in each case optionally cyano-, fluorine-, chlorine-, bromine-, methyl-, ethyl-, n- or i-propyl-substituted cyclopropyl, cyclobutyl, cyclopentyl or cyclohexyl.

$R^{20}$ preferably represents hydrogen, represents in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propinyl or butinyl, in each case optionally cyano-, fluorine-, chlorine-, bromine-, methyl-, ethyl-, n- or i-propyl-substituted cyclopropyl, cyclobutyl, cyclopentyl or cyclohexyl, or optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, or together with $R^{19}$ represents in each case optionally methyl- or ethyl-substituted butane-1,4-diyl (trimethylene), pentane-1,5-diyl, 1-oxa-butane-1,4-diyl or 3-oxa-pentane-1,5-diyl.

$X^4$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

$X^5$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

Examples of compounds of the formula (IIa) which are very particularly preferred as herbicide safeners according to the invention are listed in Table 2 below.

TABLE 2

Examples of the compounds of the formula (IIa)

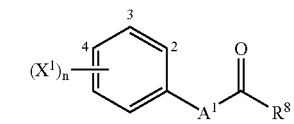

(IIa)

| Example No. | (positions) $(X^1)_n$ | $A^1$ | $R^8$ |
|---|---|---|---|
| IIa-1 | (2) Cl, (4) Cl | pyrazoline with H3C, C(O)OCH3 | OCH3 |
| IIa-2 | (2) Cl, (4) Cl | pyrazoline with H3C, C(O)OC2H5 | OCH3 |
| IIa-3 | (2) Cl, (4) Cl | pyrazoline with H3C, C(O)OCH3 | OC2H5 |
| IIa-4 | (2) Cl, (4) Cl | pyrazoline with H3C, C(O)OC2H5 | OC2H5 |
| IIa-5 | (2) Cl | pyrazole with phenyl | OCH3 |
| IIa-6 | (2) Cl, (4) Cl | pyrazole with phenyl | OCH3 |
| IIa-7 | (2) F | pyrazole with phenyl | OCH3 |
| IIa-8 | (2) F | pyrazole with 2-Cl-phenyl | OCH3 |
| IIa-9 | (2) Cl, (4) Cl | triazole with CCl3 | OC2H5 |
| IIa-10 | (2) Cl, (4) CF3 | triazole with phenyl | OCH3 |

TABLE 2-continued

Examples of the compounds of the formula (IIa)

(IIa)

$(X^1)_n$-phenyl-$A^1$-C(=O)-$R^8$ (positions 2,3,4)

| Example No. | (positions) $(X^1)_n$ | $A^1$ | $R^8$ |
|---|---|---|---|
| IIa-11 | (2) Cl | 1,3-dimethyl-pyrazol-5-yl with 2-F-phenyl | $OCH_3$ |
| IIa-12 | — | 3-methyl-5-phenyl-4,5-dihydroisoxazol-5-yl | $OC_2H_5$ |
| IIa-13 | (2) Cl, (4) Cl | 1,3-dimethyl-5-methyl-pyrazolyl ($H_3C$) | $OC_2H_5$ |
| IIa-14 | (2) Cl, (4) Cl | 1,3-dimethyl-5-isopropyl-pyrazolyl ($C_3H_7$-i) | $OC_2H_5$ |
| IIa-15 | (2) Cl, (4) Cl | 1,3-dimethyl-5-tert-butyl-pyrazolyl ($C_4H_9$-t) | $OC_2H_5$ |
| IIa-16 | (2) Cl, (4) Cl | 3-methyl-4,5-dihydroisoxazol-5-ylmethyl ($CH_2$) | $OC_2H_5$ |
| IIa-17 | (2) Cl, (4) Cl | 3-methyl-4,5-dihydroisoxazol-5-yl | $OC_2H_5$ |

Examples of compounds of the formula (IIb) which are very particularly preferred as herbicide safeners according to the invention are listed in Table 3 below.

TABLE 3

(IIb)

8-hydroxyquinoline with $X^2$ at position 5, $X^3$ at position 3, O-$A^2$-C(=O)-$R^9$ at position 8

Examples of the compounds of the formula (IIb)

| Example No. | (position) $X^2$ | (position) $X^3$ | $A^2$ | $R^9$ |
|---|---|---|---|---|
| IIb-1 | (5) Cl | — | $CH_2$ | OH |
| IIb-2 | (5) Cl | — | $CH_2$ | $OCH_3$ |
| IIb-3 | (5) Cl | — | $CH_2$ | $OC_2H_5$ |
| IIb-4 | (5) Cl | — | $CH_2$ | $OC_3H_7$-n |
| IIb-5 | (5) Cl | — | $CH_2$ | $OC_3H_7$-i |
| IIb-6 | (5) Cl | — | $CH_2$ | $OC_4H_9$-n |
| IIb-7 | (5) Cl | — | $CH_2$ | $OCH(CH_3)C_5H_{11}$-n |
| IIb-8 | (5) Cl | (2) F | $CH_2$ | OH |
| IIb-9 | (5) Cl | (2) Cl | $CH_2$ | OH |
| IIb-10 | (5) Cl | — | $CH_2$ | $OCH_2CH=CH_2$ |
| IIb-11 | (5) Cl | — | $CH_2$ | $OC_4H_9$-i |
| IIb-12 | (5) Cl | — | $CH_2$ | $OCH(CH_3)OCH_2CH(CH_2)CH=CH_2$ (allyloxy methoxy ethyl group as drawn) |
| IIb-13 | (5) Cl | — | $CH_2$ | $OCH_2CH=CH_2$ attached via $OC(=O)CH(CH_3)$- (isobutyrate of allyl) |
| IIb-14 | (5) Cl | — | $C_2H_5$ | $OC_2H_5$ (as isobutyrate ester) |

Examples of the compounds (IIc) which are very particularly preferred as herbicide safeners according to the invention are listed in Table 4 below.

TABLE 4

(IIc)

R<sup>10</sup>—C(=O)—N(R<sup>11</sup>)(R<sup>12</sup>)

Examples of the compounds of the formula (IIc)

| Example No. | $R^{10}$ | $N(R^{11}, R^{12})$ |
|---|---|---|
| IIc-1 | $CHCl_2$ | $N(CH_2CH=CH_2)_2$ |
| IIc-2 | $CHCl_2$ | 2,2-dimethyl-3-methyl-oxazolidin-3-yl |
| IIc-3 | $CHCl_2$ | 2,2,5-trimethyl-3-methyl-oxazolidin-3-yl |
| IIc-4 | $CHCl_2$ | 1-methyl-1-aza-4-oxa-spiro[4.5]decan-1-yl |
| IIc-5 | $CHCl_2$ | 2,2-dimethyl-3-methyl-5-phenyl-oxazolidin-3-yl |
| IIc-6 | $CHCl_2$ | 3,4-dimethyl-3,4-dihydro-2H-benzo[1,4]oxazin-4-yl |
| IIc-7 | $CHCl_2$ | 2,2-dimethyl-3-methyl-5-(furan-2-yl)-oxazolidin-3-yl |

TABLE 5

(IId)

Examples of the compounds of the formula (IId)

| Example No. | $R^{16}$ | $R^{17}$ | $R^{18}$ | (positions) $(X^4)_n$ | (positions) $(X^5)_n$ |
|---|---|---|---|---|---|
| IId-1 | H | H | $CH_3$ | (2) $OCH_3$ | — |
| IId-2 | H | H | $C_2H_5$ | (2) $OCH_3$ | — |
| IId-3 | H | H | $C_3H_7$-n | (2) $OCH_3$ | — |
| IId-4 | H | H | $C_3H_7$-i | (2) $OCH_3$ | — |
| IId-5 | H | H | cyclopropyl | (2) $OCH_3$ | — |
| IId-6 | H | H | $CH_3$ | (2) $OCH_3$ (5) $CH_3$ | — |
| IId-7 | H | H | $C_2H_5$ | (2) $OCH_3$ (5) $CH_3$ | — |
| IId-8 | H | H | $C_3H_7$-n | (2) $OCH_3$ (5) $CH_3$ | — |
| IId-9 | H | H | $C_3H_7$-i | (2) $OCH_3$ (5) $CH_3$ | — |
| IId-10 | H | H | cyclopropyl | (2) $OCH_3$ (5) $CH_3$ | — |
| IId-11 | H | H | $OCH_3$ | (2) $OCH_3$ (5) $CH_3$ | — |
| IId-12 | H | H | $OC_2H_5$ | (2) $OCH_3$ (5) $CH_3$ | — |
| IId-13 | H | H | $OC_3H_7$-i | (2) $OCH_3$ (5) $CH_3$ | — |
| IId-14 | H | H | $SCH_3$ | (2) $OCH_3$ (5) $CH_3$ | — |
| IId-15 | H | H | $SC_2H_5$ | (2) $OCH_3$ (5) $CH_3$ | — |
| IId-16 | H | H | $SC_3H_7$-i | (2) $OCH_3$ (5) $CH_3$ | — |
| IId-17 | H | H | $NHCH_3$ | (2) $OCH_3$ (5) $CH_3$ | — |
| IId-18 | H | H | $NHC_2H_5$ | (2) $OCH_3$ (5) $CH_3$ | — |
| IId-19 | H | H | $NHC_3H_7$-i | (2) $OCH_3$ (5) $CH_3$ | — |
| IId-20 | H | H | NH-cyclopropyl | (2) $OCH_3$ (5) $CH_3$ | — |
| IId-21 | H | H | $NHCH_3$ | (2) $OCH_3$ | — |
| IId-22 | H | H | $NHC_3H_7$-i | (2) $OCH_3$ | — |
| IId-23 | H | H | $N(CH_3)_2$ | (2) $OCH_3$ | — |
| IId-24 | H | H | $N(CH_3)_2$ | (3) $CH_3$ (4) $CH_3$ | — |

Examples of the compounds of the formula (IId) which are very particularly preferred as herbicide safeners according to the invention are listed in Table 5 below.

Examples of the compounds of the formula (IIe) which are very particularly preferred as herbicide safeners according to the invention are listed in Table 6 below.

TABLE 6

(IIe)

Examples of the compounds of the formula (IIe)

| Example No. | $R^{16}$ | $R^{19}$ | $R^{20}$ | (positions) $(X^4)_n$ | (positions) $(X^5)_n$ |
|---|---|---|---|---|---|
| IIe-1 | H | H | $CH_3$ | (2) $OCH_3$ | — |
| IIe-2 | H | H | $C_2H_5$ | (2) $OCH_3$ | — |
| IIe-3 | H | H | $C_3H_7$-n | (2) $OCH_3$ | — |
| IIe-4 | H | H | $C_3H_7$-i | (2) $OCH_3$ | — |
| IIe-5 | H | H | cyclopropyl | (2) $OCH_3$ | — |
| IIe-6 | H | $CH_3$ | $CH_3$ | (2) $OCH_3$ | — |
| IIe-7 | H | H | $CH_3$ | (2) $OCH_3$ | (5) $CH_3$ |
| IIe-8 | H | H | $C_2H_5$ | (2) $OCH_3$ | (5) $CH_3$ |
| IIe-9 | H | H | $C_3H_7$-n | (2) $OCH_3$ | (5) $CH_3$ |
| IIe-10 | H | H | $C_3H_7$-i | (2) $OCH_3$ | (5) $CH_3$ |
| IIe-11 | H | H | cyclopropyl | (2) $OCH_3$ | (5) $CH_3$ |
| IIe-12 | H | $CH_3$ | $CH_3$ | (2) $OCH_3$ | (5) $CH_3$ |

Most preferred compounds which improve crop plant compatibility [component (b)] are cloquintocet-mexyl, fenchlorazole-ethyl, isoxadifen-ethyl, mefenpyr-diethyl, furilazole, fenclorim, cumyluron, dymron, dimepiperate and the compound IIe-11, and particular emphasis is given to cloquintocet-mexyl and mefenpyr-diethyl.

Examples of the selectively herbicidal combinations according to the invention of in each case one active compound of the formula (I) and in each case one of the safeners defined above are listed in Table 7 below.

TABLE 7

Examples of combinations according to the invention

| Active compound of the formula (I) | Safener |
|---|---|
| I-1 | cloquintocet-mexyl |
| I-1 | fenchlorazole-ethyl |
| I-1 | isoxadifen-ethyl |
| I-1 | mefenpyr-diethyl |
| I-1 | furilazole |
| I-1 | fenclorim |
| I-1 | cumyluron |
| I-1 | daimuron/dymron |
| I-1 | dimepiperate |
| I-1 | IIe-11 |
| I-2 | cloquintocet-mexyl |
| I-2 | fenchlorazole-ethyl |
| I-2 | isoxadifen-ethyl |
| I-2 | mefenpyr-diethyl |
| I-2 | furilazole |
| I-2 | fenclorim |
| I-2 | cumyluron |
| I-2 | daimuron/dymron |
| I-2 | dimepiperate |
| I-2 | IIe-11 |
| I-3 | cloquintocet-mexyl |
| I-3 | fenchlorazole-ethyl |
| I-3 | isoxadifen-ethyl |
| I-3 | mefenpyr-diethyl |
| I-3 | furilazole |
| I-3 | fenclorim |
| I-3 | cumyluron |
| I-3 | daimuron/dymron |
| I-3 | dimepiperate |
| I-3 | IIe-11 |
| I-4 | cloquintocet-mexyl |
| I-4 | fenchlorazole-ethyl |
| I-4 | isoxadifen-ethyl |
| I-4 | mefenpyr-diethyl |
| I-4 | furilazole |
| I-4 | fenclorim |
| I-4 | cumyluron |
| I-4 | daimuron/dymron |
| I-4 | dimepiperate |
| I-4 | IIe-11 |
| I-5 | cloquintocet-mexyl |
| I-5 | fenchlorazole-ethyl |
| I-5 | isoxadifen-ethyl |
| I-5 | mefenpyr-diethyl |
| I-5 | furilazole |
| I-5 | fenclorim |
| I-5 | cumyluron |
| I-5 | daimuron/dymron |
| I-5 | dimepiperate |
| I-5 | IIe-11 |
| I-6 | cloquintocet-mexyl |
| I-6 | fenchlorazole-ethyl |
| I-6 | isoxadifen-ethyl |
| I-6 | mefenpyr-diethyl |
| I-6 | furilazole |
| I-6 | fenclorim |
| I-6 | cumyluron |
| I-6 | daimuron/dymron |
| I-6 | dimepiperate |
| I-6 | IIe-11 |

Surprisingly, it has now been found that the above-defined active compound combinations of substituted cyclic ketoenols of the general formula (I) and safeners (antidotes) of group (b) listed above, whilst being tolerated very well by crop plants, have particularly high herbicidal activity and can be used in various crops, in particular in cereal (especially wheat), but also in soya beans, potatoes, maize and rice, for the selective control of weeds.

Here, it has to be considered to be surprising that, from a large number of known safeners or antidotes which are capable of antagonizing the damaging effect of a herbicide on the crop plants, it is in particular the abovementioned compounds of group (b) which neutralize the damaging effect of substituted cyclic ketoenols on the crop plants virtually completely without negatively affecting the herbicidal activity with respect to the weeds.

Emphasis is given here to the particularly advantageous effect of the particularly and most preferred combination partners from group (b), in particular in respect of sparing cereal plants, such as, for example, wheat, barley and rye, but also maize and rice, as crop plants.

The active compound combinations according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Cardus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cuburbita, Helianthus.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera.

Monocotyledonous crops of the genera: Oryza, Zea, Triticum, Hordeum, Avena, Secale, Sorghum, Panicum, Saccharum, Ananas, Asparagus, Allium.

However, the use of the active compound combinations according to the invention is in no way restricted to these genera, but also extends in the same manner to other plants.

According to the invention, it is possible to treat all plants and parts of plants. Here, plants are to be understood as meaning all plant and plant populations such as desirable and undesirable wild plants or crop plants (including naturally occurring crop plants). Crop plants can be plants which are obtained by conventional breeding and optimization methods or by biotechnological and recombinant methods or combinations of these methods, including the transgenic plants and including the plant cultivars which can or cannot be protected by breeders' rights. Plant parts are to be understood as meaning all above-ground and below-grounds parts and organs of the plants, such as shoots, leaves, flowers and roots, where leaves, needles, stems, trunks, flowers, fruit bodies, fruits and seeds and also roots, tubers and rhizomes may be mentioned by way of example. Plant parts also include harvested produce and vegetative and generative propagation material, for example seedlings, tubers, rhizomes, cuttings and seeds.

The treatment according to the invention of the plants and plant parts with the active compounds is carried out directly or by action on their environment, habitat or storage space by customary treatment methods, for example by dipping, spraying, evaporating, atomizing, broadcasting, spreading-on and, in the case of propagation material, in particular in the case of the seeds, furthermore by applying one or more coats.

The advantageous effect of the crop plant compatibility of the active compound combinations according to the invention is particularly highly pronounced at certain concentration ratios. However, the weight ratios of the active compounds in the active compound combinations can be varied within relatively wide ranges. In general, 0.001 to 1000 parts by weight, preferably 0.01 to 100 parts by weight, particularly preferably 0.05 to 10 parts by weight and most preferably 0.07 to 1.5 parts by weight of one of the compounds which improve crop plant compatibility mentioned under (b) above (antidotes/safeners) are present per part by weight of active compound of the formula (I) or its salts.

The active compounds or active compound combinations can be converted into the customary formulations, such as solutions, emulsions, wettable powders, suspensions, powders, dusting agents, pastes, soluble powders, granules, suspoemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to use, for example, organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are:

for example ammonium salts and ground natural minerals, such as kaolins, clays, talc, chalk, quartz, attapulgite, montmorillonite or diatomaceous earth, ground synthetic minerals, such as finely divided silica, alumina and silicates, suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example non-ionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and protein hydrolysates; suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise from 0.1 to 95 percent by weight of active compounds including the safeners, preferably between 0.5 and 90%.

The active compound combinations according to the invention are generally used in the form of finished formulations. However, the active compounds contained in the active compound combinations can also be mixed in individual formulations when used, i.e. in the form of tank mixes.

The novel active compound combinations, as such or in their formulations, can furthermore be used as a mixture with other known herbicides, finished formulations or tank mixes again being possible. A mixture with other known active compounds, such as fungicides, insecticides, acaricides, nematicides, bird repellents, growth factors, plant nutrients and agents which improve soil structure, is also possible. For certain intended uses, in particular in the post-emergence method, it may furthermore be advantageous to include, as further additives in the formulations, mineral or vegetable oils which are tolerated by plants (for example the commercial preparation "Rako Binol"), or ammonium salts such as, for example, ammonium sulfate or ammonium thiocyanate.

The novel active compound combinations can be used as such, in the form of their formulations or the use forms prepared therefrom by further dilution, such as ready-to-use solutions, suspensions, emulsions, powders, pastes and granules. They are used in the customary manner, for example by washing, spraying, atomizing, dusting or scattering.

The amounts of the active compound combinations according to the invention applied can be varied within a certain range; they depend, inter alia, on the weather and on soil factors. In general, the application rates are between 0.005 and 5 kg per ha, preferably between 0.01 and 2 kg per ha, particularly preferably between 0.05 and 1.0 kg per ha.

The active compound combinations according to the invention can be applied before and after emergence of the plants, that is to say by the pre-emergence and post-emergence method.

USE EXAMPLES

The active compound or safener components are in each case dissolved in a few ml (generally 2-3 ml) of solvent (generally acetone or N,N-dimethyl-formamide), and the solutions are combined and then—if appropriate after addition of an emulsifier—diluted with water to the desired concentration. In general, an aqueous spray liquor was prepared using 0.1% of the additive Renex-36.

Example A

Post-Emergence Test

The test plants are grown under controlled conditions (temperature, light, atmospheric humidity) in a greenhouse. The test plants are sprayed when they have reached a height of 5-15 cm. The concentration of the spray liquor is chosen such that the particular amounts of active compound desired are applied in 500 l of water/ha.

After spraying, the pots with the test plants are kept in a greenhouse chamber under controlled conditions (temperature, light, atmospheric humidity) until the test has ended. About three weeks after the application, the degree of damage to the crop plants is rated in % damage in comparison to the development of the untreated control.

The figures denote:

0% no damage (like untreated control)

100% total destruction/damage

Active compounds, application rates, test plants and results are shown in the tables below, the terms being used in the tables being as defined below:

Active Compounds

Example I-1-a-1

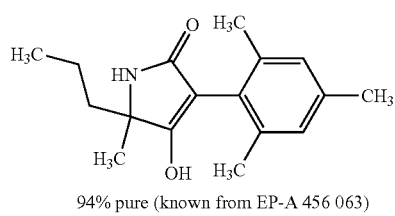

94% pure (known from EP-A 456 063)

Example I-1-a-2

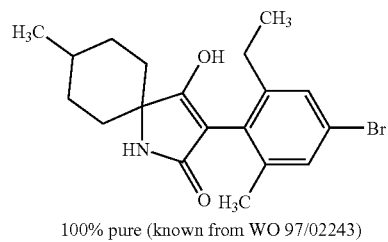

100% pure (known from WO 97/02243)

Example I-1-a-3

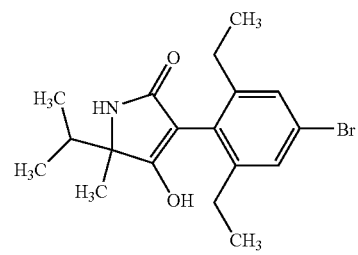

99% pure (known from WO 97/02243)

Example I-1-a-4

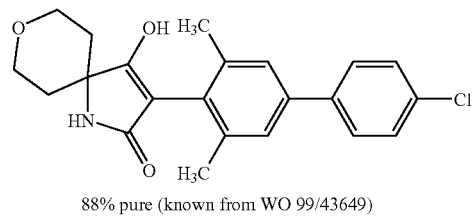

88% pure (known from WO 99/43649)

Mefenpyr-diethyl (used as 100 EC)
Cloquintocet-mexyl, 99% pure

TABLE A-1

| | Application rate g of ai/ha | Winter barley observed |
|---|---|---|
| Example I-1-a-1 | 440 | 70 |
| | 220 | 25 |
| | 110 | 10 |
| Example I-1-a-1 + mefenpyr-diethyl | 440 + 50 | 15 |
| | 220 + 50 | 10 |
| | 110 + 50 | 0 |

TABLE A-2

| | Application rate g of ai/ha | Winter wheat observed |
|---|---|---|
| Example I-1-a-2 | 125 | 10 |
| Example I-1-a-2 + mefenpyr-diethyl | 125 + 50 | 5 |

TABLE A-3

| | Application rate g of ai/ha | Winter barley observed |
|---|---|---|
| Example I-1-a-2 | 250 | 65 |
| | 125 | 20 |
| Example I-1-a-2 + mefenpyr-diethyl | 250 + 50 | 50 |
| | 125 + 50 | 10 |

TABLE A-4

| | Application rate g of ai/ha | Winter wheat observed |
|---|---|---|
| Example I-1-a-3 | 250 | 15 |
| | 125 | 10 |
| Example I-1-a-3 + mefenpyr-diethyl | 250 + 50 | 0 |
| | 125 + 50 | 0 |

TABLE A-5

| | Application rate g of ai/ha | Winter barley observed |
|---|---|---|
| Example I-1-a-4 | 250 | 35 |
| | 125 | 35 |
| | 60 | 5 |
| Example I-1-a-4 + mefenpyr-diethyl | 250 + 50 | 5 |
| | 125 + 50 | 0 |
| | 60 + 50 | 0 |

TABLE A-6

| | Application rate g of ai/ha | Winter barley observed | Winter wheat observed |
|---|---|---|---|
| Mefenpyr-diethyl | 50 | 0 | 0 |

TABLE A-7

| | Application rate g of ai/ha | Winter barley observed |
|---|---|---|
| Example I-1-a-1 | 440 | 70 |
| | 220 | 25 |
| | 110 | 10 |
| Example I-1-a-1 + cloquintocet-mexyl | 440 + 50 | 10 |
| | 220 + 50 | 5 |
| | 110 + 50 | 5 |

TABLE A-8

| | Application rate g of ai/ha | Winter wheat observed |
|---|---|---|
| Example I-1-a-2 | 250 | 40 |
| Example I-1-a-2 + cloquintocet-mexyl | 250 + 50 | 15 |

TABLE A-9

| | Application rate g of ai/ha | Winter barley observed |
|---|---|---|
| Example I-1-a-2 | 250 | 65 |
| | 125 | 20 |
| | 60 | 5 |

TABLE A-9-continued

| | Application rate g of ai/ha | Winter barley observed |
|---|---|---|
| Example I-1-a-2 + cloquintocet-mexyl | 250 + 50 | 15 |
| | 125 + 50 | 5 |
| | 60 + 50 | 0 |

TABLE A-10

| | Application rate g of ai/ha | Winter barley observed |
|---|---|---|
| Example I-1-a-3 | 250 | 40 |
| Example I-1-a-3 + cloquintocet-mexyl | 250 + 50 | 30 |

TABLE A-11

| | Application rate g of ai/ha | Winter barley observed |
|---|---|---|
| Example I-1-a-4 | 250 | 35 |
| | 125 | 35 |
| Example I-1-a-4 + cloquintocet-mexyl | 250 + 50 | 10 |
| | 125 + 50 | 10 |

TABLE A-12

| | Application rate g of ai/ha | Winter wheat observed | Winter barley observed |
|---|---|---|---|
| cloquintocet-mexyl | 50 | 0 | 0 |

The invention claimed is:

1. A composition comprising an effective amount of an active compound combination comprising
   (a) at least one substituted cyclic ketoenol of formula (I)

(I)

[Structure: CKE connected to a benzene ring with substituents X, Y, Z, W]

including any tautomeric forms thereof or a salt or an acid or base adduct of the compounds of formula (I) including any tautomeric forms thereof, in which X represents chlorine, bromine, methyl, ethyl, propyl, vinyl, ethynyl, methoxy, ethoxy, trifluoromethyl, difluoromethoxy, trifluoromethoxy, or cyano, Z represents hydrogen, vinyl, or ethynyl; or represents the radical

[Structure: benzene ring with substituents $V^1$ and $V^2$]

in which
   $V^1$ represents hydrogen, fluorine, chlorine, bromine, methyl, ethyl, n-propyl, isopropyl, n-butyl, isobutyl, tert-butyl, methoxy, ethoxy, n-propoxy, isopropoxy, trifluoromethyl, trifluoromethoxy, trifluoroethoxy, or cyano, and V² represents hydrogen, fluorine, chlorine, methyl, ethyl, n-propyl, isopropyl, methoxy, ethoxy, trifluoromethyl, or trifluoromethoxy, W and Y independently of one another represent hydrogen, fluorine, chlorine, bromine, methyl, ethyl, n-propyl, methoxy, or ethoxy, with the proviso that W and X do not simultaneously represent ethyl when Y represents 4-methyl and W does not represent methoxy or difluoromethoxy when X represents ethyl, and with the further proviso that X does not represent vinyl or ethynyl if Z does not represent hydrogen, and CKE represents

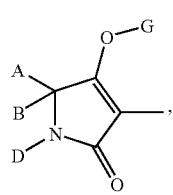

(1)

in which

A represents hydrogen; represents C₁-C₄-alkyl or C₁-C₂-alkoxy-C₁-C₂-alkyl, each of which is optionally mono- to trisubstituted by fluorine; or represents C₃-C₆-cycloalkyl that is optionally monosubstituted by fluorine, methyl, ethyl, or methoxy, B represents hydrogen, methyl, or ethyl, D represents hydrogen, and G represents hydrogen (a) or represents one of the groups

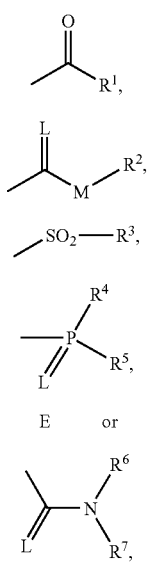

in which

E represents a metal ion equivalent or an ammonium ion,

L represents oxygen,

M represents oxygen or sulphur,

R¹ represents C₁-C₁₀-alkyl, C₂-C₁₀-alkenyl, C₁-C₄-alkoxy-C₁-C₂-alkyl, C₁-C₄-alkylthio-C₁-C₂-alkyl, each of which is optionally mono- to trisubstituted by fluorine or chlorine; or represents C₃-C₆-cycloalkyl which is optionally mono- to trisubstituted by fluorine, chlorine, methyl, ethyl, or methoxy; represents phenyl that is optionally mono- or disubstituted by fluorine, chlorine, bromine, cyano, nitro, methyl, methoxy, trifluoromethyl, or trifluoromethoxy, R² represents C₁-C₁₀-alkyl, C₂-C₁₀-alkenyl, or C₁-C₄-alkoxy-C₂-C₄-alkyl, each of which is optionally mono- to trisubstituted by fluorine; represents C₃-C₆-cycloalkyl that is optionally monosubstituted by fluorine, methyl, or methoxy; or represents phenyl or benzyl, each of which is optionally mono- or disubstituted by fluorine, chlorine, cyano, nitro, methyl, methoxy, trifluoromethyl, or trifluoromethoxy, R³ represents methyl, ethyl, n-propyl, or isopropyl, each of which is optionally mono- to trisubstituted by fluorine; or represents phenyl that is optionally monosubstituted by fluorine, chlorine, bromine, methyl, tert-butyl, methoxy, trifluoromethyl, trifluoromethoxy, cyano, or nitro, R⁴ represents C₁-C₄-alkyl, C₁-C₄-alkoxy, C₁-C₄-alkylamino, di-(C₁-C₄-alkyl)amino, or C₁-C₄-alkylthio; or represents phenyl, phenoxy, or phenylthio, each of which is optionally monosubstituted by fluorine, chlorine, bromine, nitro, cyano, C₁-C₂-alkoxy, C₁-C₂-fluoroalkoxy, C₁-C₂-alkylthio, C₁-C₂-fluoroalkylthio, or C₁-C₃-alkyl, R⁵ represents C₁-C₃-alkoxy or C₁-C₃-alkylthio, R⁶ represents hydrogen; represents C₁-C₄-alkyl, C₃-C₆-cycloalkyl, C₁-C₄-alkoxy, C₃-C₄-alkenyl, OR C₁-C₄-alkoxy-C₁-C₄-alkyl; represents phenyl that is optionally mono- or disubstituted by fluorine, chlorine, bromine, trifluoromethyl, methyl, or methoxy; or represents benzyl that is optionally monosubstituted by fluorine, chlorine, bromine, methyl, trifluoromethyl, or methoxy, and R⁷ represents C₁-C₄-alkyl, C₃-C₄-alkenyl, or C₁-C₄-alkoxy-C₁-C₂-alkyl, or R⁶ and R⁷ together represent a C₅-C₆-alkylene radical in which one methylene group is optionally replaced by oxygen or sulphur, and (b) at least one compound that improves crop plant compatibility selected from the compounds 1-methyl-hexyl 5-chloro-quinolin-8-oxy-acetate (cloquintocet-mexyl) and diethyl 1-(2,4-dichloro-phenyl)-4,5-dihydro-5-methyl-1H-pyrazole-3,5-dicarboxylate (mefenpyr-diethyl).

2. A composition according to claim 1 in which, in formula (I), Z represents hydrogen and Y is located in the position para to the group CKE, or in which Z represents the group

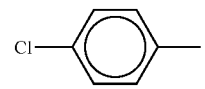

in the position para or meta to the group CKE.

3. A composition according to claim 1 wherein from 0.05 to 10 parts by weight of the compound that improves crop plant compatibility are present per part by weight of the active compound of the formula (I).

4. A method for controlling undesirable vegetation comprising allowing an effective amount of a composition according to claim 1 to act on plants and/or their habitat.

* * * * *